United States Patent [19]

Greene, Jr. et al.

[11] Patent Number: 4,770,184
[45] Date of Patent: Sep. 13, 1988

[54] ULTRASONIC DOPPLER DIAGNOSTIC SYSTEM USING PATTERN RECOGNITION

[75] Inventors: Francis M. Greene, Jr., Seattle; Donald E. Strandness, Jr., Bellevue, both of Wash.

[73] Assignee: Washington Research Foundation, Seattle, Wash.

[21] Appl. No.: 810,872

[22] Filed: Dec. 17, 1985

[51] Int. Cl.$^4$ ............................................. A61B 10/00
[52] U.S. Cl. ................................................. 128/661.08
[58] Field of Search .................... 128/663; 73/861.25; 364/417

[56] References Cited

U.S. PATENT DOCUMENTS

| | | | |
|---|---|---|---|
| 4,062,237 | 12/1977 | Fox | 73/194 A |
| 4,109,642 | 8/1978 | Reid et al. | 128/2 |
| 4,324,258 | 4/1982 | Huebscher et al. | 128/663 |

OTHER PUBLICATIONS

Greene, et al., "Computer Based Pattern Recognition of Carotid Arterial Disease Using Pulsed Doppler Ultrasound", Ultrasound Med. Biol., 8(2), 161-76.
P. Breslau et al., "Evaluation of Carotid Bifurcation Disease: The Role of Common Carotid Artery Velocity Patterns," Arch. Surg., Jan. 1982, 117, 56-60.
P. Breslau et al., "Effect of Carbon Dioxide on Flow Patterns in Normal Extracranial Arteries," J. Surg. Res. 32, 97-103, (1982).
K. Adiga, et al., "Noninvasive Methods in the Diagnosis of Extracranial Carotid Artery Disease: A Correlation with Carotid Arterigraphy in eighy Patients," Angiloogy, Jum. 1984, 35(6), 331-40.
W. Blackshear, Jr., et al., "Correlation of Hemodynamically Significant Internal Carotid Stenosis with Pulsed Doppler Frequency Analysis," Ann. Surg., Apr. 1984, 199(4), 475-81.
J. Murie, et al., "Carotid Artery Bruit: Association with Internal Carotid Stenosis and Intraluminal Turbulence," Br. J. Surg., Jan. 1984, 71 (1), 50-2.
J. Murie, et al., "Pulsed Doper Imaging and Spectrum Analysis for Detection of Carotid Artery Disease," Angiology, Apr. 1984, 35(4), 215-21.
P. Benedic, et al., "Comparison of Ultrasound Scanning/Doppler with Digital Subtraction Angiography in Evaluating Carotid Arterial Disease Med. Instrum., May-Jun. 1983, 17(3), 220-2.
K. Garth, et al., "Duplex Ulrasound Scanning of the Carotid Arteries with Velocity Spectrum Analysis," Radioloy, Jun, 1983, 147(3), 823-7.
J. Murie et al., "Pulsed Doppler Imaging for Carotid Artery Disease,".
Scott Med. J. (Scotland), Jan. 1983, 28(1), 21-4.
W. Blackshear, Jr. et al., "Carotid Endarterectomy without Angiography."
J. Cardiovasc. Surg. (Torino), Nov.-Dec. 1982, 23(6), 477-82.
B. Keagy, et al., "Objectiv Criteria for the Interpretation of Carotid Artery Spectral Analysis Patterns."Angiology, Apr. 1982, 33(4) 213-20.
B. Diebold et al, "Nonevasive Assessment of Aortocoronary Bypass Graft Patency Using Pulsed Doppler Echocardiography,"Am. J. Cardiol., Jan. 1979, 43(1), 10-6.

(List continued on next page.)

*Primary Examiner*—Francis J. Jaworski
*Attorney, Agent, or Firm*—Christensen, O'Connor, Johnson & Kindness

[57] ABSTRACT

A frequency-analyzed signal from a pulsed Doppler ultrasound examination is processed in a dedicated computer using statistical pattern recognition to assess the presence and extent of arterial disease. The Doppler blood flow signal is derived from a suitable utlrasound scanner, is frequency analyzed with a real-time, fast Fourier Transformer spectrum analyzer, and is processed by the computer to achieve a diagnosis of the degree of stenosis of the carotid artery through pattern recognition between the Doppler signal and a database of known preclassified spectra. The diagnosis ordinarily follows a hierarchical decision making format to objectively classify the condition of the patient.

4 Claims, 2 Drawing Sheets

OTHER PUBLICATIONS

R. Lewis et al., "Imaging the Carotid Bifurcation Using Continuous-Wave Doppler-Shift Ultrasound and Spectral Analysis," Stroke Sep.-Oct. 1978,. 9(5), 465-71.

C. Roberts, "Ultrasound in the Assessment of Vascular Function," Med. Prog. Technol, Jul. 76 1920, 4(1-2), 3-10.

H. Keller, et al., "Nonevasive Measurement of Velocity Profiles and Blood Flow in the Common Carotid Artery Pulsed Doppler Ultrasound," Stroke, Jul.-Aug. 1976, 7(4), 370-7.

R. Barnes, et al., "Nonevasive Ultrasonic Carotid Angiography: Perspective Validation by Contrasr Arterography," Surgery, Sep. 1976, 80(3) 328-35.

R. Felix, Jr. et al., "Pulsed Dopper Ultrasound Detection of Flow Disturbances in Arteriosclerosis," J. Clin. Ultrasound, Aug. 1976, 4(4) 275-8.

C. Joyner, "Transcutaneous Dopler Detector in the Study of Arterial and Venous Flow Patterns," Cardiovasc. Clin. 1975, 6 (3) 275-99.

H. Brunner, et al., "Bestimmung Instantaner Stromungsgeschwindigkeitspro file in der A. fermoraliscommunis mit gepulstem Dopper-Ultraschall.

bei Stenosen and Verschlussen der Beckenarterien, "Dtsch. Med. Wochenschr Jan. 4, 1974, 99(1), 3-7.

D. Baker et al., "Pulsed Doppler Techiques: Some Examples from the Univ. of Washington, "Ultrasound Med. Biol., 2(4) 251-62 (1977)/*Y. Langlois et al., "Evaulating Carotid Artery Disease. The Concordance Between Pulsed Doppler/Spectrum Analysis and Angiography," Ultrasound Med. Biol., Jan-Feb. 1983, 9(1), 51-63.*

R. Knox et al., "Computer Based Clasificaitn of Carotid Arterial Disease: A Prospective Assessment," Stroke Sep.-Oct. 1982, 13, 589-94.

F. Greene, et al., "Computer Based Pattern Recognition of Carotid Arterial Disease Using Pulsed Doppler Ultrasound," Ultrasound Med. Biol., 8(2), 161-76.

*K. Bodily et al., "Spectral Analysis of Dopper Velocity Patterns inNormals and Patients with Carotid Artery Stenosis," Clin. Physiol., Aug. 1981, 1(4), 365-74.*

Y. Langlois et al., "The Use of Common Carotid Waveform Analysis in the Diagnosis of Carotid Occlusive Disease," Angiology, Oct. 1983.

D. Phillips et al., "Flow Velocity Patterns in the Carotid Bifurcations of Yung, Pesumed Normal Subjects," Ultrasound Med. Biol. Jan-Feb. 1983, 9(1), G. Fell et al.," Ultrasonic Duplex Scanning for Disease of the Carotid Artery," Circulation, Dec. 1981, 64(6) 1191-5.

W. Blackshear, Jr. et al, Ultrasonic Demonstration of External and Internal Carotid Patency with Common Carotid Occlusion: A Preliminary Report," MayJun 1980, 11(3), 249-52.

W. Blackshear, Jr. et al., "Carotid Artery Velocity Patterns in Normal and Stenotic Vessels," Stroke, Jan--Feb. 1980 11(1), 67-71.

W. Blackshear, Jr. et al., "Detection of Carotid Occlusive Disease by Ultrasonic Imaging and Pulsed Doppler Spectrum Analysis," Surgery, Nov. 1979, 86(5) 698-706, P. Breslau et al.," Evaulatin of Carotid Bifurcation Disease: The Role of Common Carotid Artery Velocity Patterns," Arch. Surg. Jan. 1982, 117-58-60.

R. Knox et al.," Emprical Findings Relating Sample Volume Size to Diagnostic Accuracy in Pulsed Doppler Cerebrovascular Studies,".

J. Clin. Ultrasound, May-Jun. 1982 10, 277-232. P. Breslau, et al., "Effects of Carbon Dioxide on Flow Patterns in Normal Extracranial Arteries," J. Surg. Res. 32, 97-103 (1982). W. Hass, et al., "Joint Study of Extracranial Occlusion-II. Arteriography, Techniques, Sites and Complications," JAMA 203, 159-166 (1968).

D. Phillips et al., "Detection of Peripheral Vascular Disease Using the Duplex Scanner III" Ultrasound Med. Biol. 6, 205-218 (1980). R. Rutherford et al., The Use of Velocity Waveform Analysis in the Diagnosis of Carotid Artery Occlusive Disease, Surgery 695-702 (1977). R. Lerski et al., Computer Analysis of Ultrasonic Signals in Diffuse Liver Disease, Ultrasound Med. Biol., 5, 341-350 (1979).

"Mathematical Feature Extration Applied to the Entire Doppler Shifted Frequency Signal Obtained from the Common Carotid Artery." Susan B. Sheriff et al. A two Page Publication.

"Studies of Blood Flow Employing Duplex, Pulsed Dopper Real-Time Sonography" Europ J Radiol, 3(1983), by Everette James Jr. et al., a four page publication.

ULTRASONIC DOPPLER DIAGNOSTIC SYSTEM USING PATTERN RECOGNITION

ACKNOWLEDGMENT

This research was generously supported by NIH grants 20898 and 20381 and by LaFoundation de la Recherche en Chirurgie de Montreal.

REFERENCE TO RELATED DOCUMENTS

I. Patents

1. Said et al., "Apparatus for Ultrasonic Arteriography," U.S. Pat. No. 4,109,642, Aug. 29, 1978.
2. Huebscher et al., "Ultrasonic Doppler Flowmeters," U.S. Pat. No. 4,324,258, Apr. 13, 1982.
3. Fox, "Crossed Beam Ultrasonic Flowmeter," U.S. Pat. No. 4,062,237, Dec. 13, 1977.

II. Technical Articles

1. K. Adiga, et al., "Noninvasive Methods in the Diagnosis of Extracranial Carotid Artery Disease: A Correlation with Carotid Arteriography in Eighty Patients" *Angiology*, June 1984, 35(6), 331–40.
2. W. Blackshear, Jr., et al., "Correlation of Hemodynamically Significant Internal Carotid Stenosis with Pulsed Doppler Frequency Analysis," *Ann. Surg.*, April 1984, 199(4), 475–81.
3. J. Murie, et al., "Pulsed Doppler Imaging and Spectrum Analysis for Detection of Carotid Artery Disease," *Angiology*, April 1984, 35(4), 215–21.
4. J. Murie, et al., "Carotid Artery Bruit: Association with Internal Carotid Stenosis and Intraluminal Turbulence," *Br. J. Surg.*, January 1984, 71(1), 50–2.
5. A. James, Jr., et al., "Studies of Blood Flow Employing Duplex, Pulsed Doppler Real-Time Sonography," *Eur. J. Radiol.*, August 1983, 3 Suppl. 1, 268–72.
6. P. Bendick, et al., "Comparison of Ultrasound Scanning/Doppler with Digital Subtraction Angiography in Evaluating Carotid Arterial Disease," *Med. Instrum.*, May–June 1983, 17(3), 220–2.
7. K. Garth, et al., "Duplex Ultrasound Scanning of the Carotid Arteries with Velocity Spectrum Analysis," *Radiology*, June 1983, 147(3), 823–7.
8. J. Murie, et al., "Pulsed Doppler Imaging for Carotid Artery Disease," *Scott Med. J.* (Scotland), January 1983, 28(1), 21–4.
9. W. Blackshear, Jr., et al., "Carotid Endarterectomy without Angiography," *J. Cardiovasc. Surg.* (Torino), November–December 1982, 23(6), 477–82.
10. L. D'Juna, et al., "In Vitro Doppler Detection of Axisymmetric Stenoses from Transverse Velocity Measurements," *J. Biomech.*, 1982, 15(9), 647–60.
11. T. Doorly, et al., "Carotid Ultrasonic Arteriography Combined with Real-Time Spectral Analysis: A Comparison with Angiography," *J. Cardiovasc. Surg.* (Torino), May–June 1982, 23(3), 243–6.
12. B. Keagy, et al., "Objective Criteria for the Interpretation of Carotid Artery Spectral Analysis Patterns," *Angiology*, April 1982, 33(4), 213–20.
13. B. Diebold et al., "Noninvasive Assessment of Aortocoronary Bypass Graft Patency Using Pulsed Doppler Echocardiography," *Am. J. Cardiol.*, January 1979, 43(1), 10–6.
14. R. Lewis et al., "Imaging the Carotid Bifurcation using Continuous-Wave Doppler-Shift Ultrasound and Spectral Analysis," *Stroke*, September–October 1978, 9(5), 465–71.
15. Noninvasive Cardiovascular Diagnosis (Monograph), NLM Call No. W3 IN1263 1st 1977n.
16. C. Roberts, "Ultrasound in the Assessment of Vascular Function," *Med. Prog. Technol.*, July 76 1920, 4(102), 3–10.
17. H. Keller, et al., "Noninvasive Measurement of Velocity Profiles and Blood Flow in the Common Carotid Artery by Pulsed Doppler Ultrasound," *Stroke*, July–August 1976, 7(4), 370–7.
18. R. Barnes, et al., "Noninvasive Ultrasonic Carotid Angiography: Prospective Validation by Contrast Arteriography," *Surgery*, September 1976, 80(3), 328–35.
19. R. Felix, Jr., et al., "Pulsed Doppler Ultrasound Detection of Flow Disturbances in Arteriosclerosis," *J. Clin. Ultrasound*, August 1976, 4(4), 275–82.
20. C. Joyner, "Transcutaneous Doppler Detector in the Study of Arterial and Venous Flow Patterns," *Cardiovasc. Clin.*, 1975, 6(3), 385–99.
21. H. Brunner, et al., "Bestimmung instantaner Stromungsgeschwindigkeitsprofile in der *A. Femoralis Communis* mit gepulstem Doppler-Ultraschall bei Stenosen and Verschlussen der Beckenarterien," *Dtsch. Med. Wochenschr*, 4 January 1974, 99(1), 3–7.
22. D. Strandness et al., "Clinical Applications of Continuous Wave and Pulsed Doppler Velocity Detectors," Velocimetrie Ultrasonore Doppler (Monograph), NLM Call No. WC 106 V443, 1974.
23. D. Baker et al., "Pulsed Doppler Techniques: Some Examples from the University of Washington," *Ultrasound Med Biol.*, 2(4), 251–62 (1977).
24. Y. Langlois et al., "Evaluating Carotid Artery Disease. The Concordance Between Pulsed Doppler/Spectrum Analysis and Angiography," *Ultrasound Med. Biol.*, January–Feburary 1983, 9(1), 51–63.
25. R. Knox. et al., "Computer Based Classification of Carotid Arterial Disease: A Prospective Assessment," *Stroke*, September–October 1982, 13, 589–94.
26. F. Greene et al., "Computer Based Pattern Recognition of Carotid Arterial Disease Using Pulsed Doppler Ultrasound," *Ultrasound Med. Biol*, 8(2), 161–76.
27. K. Bodily et al., "Spectral Analysis of Doppler Velocity Patterns in Normals and Patients with Carotid Artery Stenosis," *Clin. Physiol.*, August 1981, 1(4), 365–74.
28. Y. Langlois et al., "The Use of Common Carotid Waveform Analysis in the Diagnosis of Carotid Occlusive Disease," *Angiology*, October 1983, 34(10), 679–87.
29. D. Phillips et al., "Flow Velocity Patterns in the Carotid Bifurcations of Young, Presumed Normal Subjects," *Ultrasound Med. Biol.*, January–Feburary 1983, 9(1), 39–49.
30. G. Fell et al., "Ultrasonic Duplex Scanning for Disease of the Carotid Artery," *Circulation*, December 1981, 64(6), 1191–5.
31. W. Blackshear, Jr., et al., "Ultrasonic Demonstration of External and Internal Carotid Patency with Common Carotid Occlusion: A preliminary Report," *Stroke*, May–June 1980, 11(3), 249–52.
32. W. Blackshear, Jr., et al., "Carotid Artery Velocity Patterns in Normal and Stenotic Vessels," *Stroke*, January–Feburary 1980, 11(1), 67–71.
33. W. Blackshear, Jr., et al., "Detection of Carotid Occlusive Disease by Ultrasonic Imaging and Pulsed Doppler Spectrum Analysis," *Surgery*, November 1979, 86(5), 698–706.
34. P. Breslau et al., "Evaluation of Carotid Bifurcation Disease: The Role of Common Carotid Artery Velocity Patterns," *Arch. Surg.*, January 1982, 117, 58-60.

35. R. Knox et al., "Empirical Findings Relating Sample Volume Size to Diagnostic Accuracy in Pulsed Doppler Cerebrovascular Studies," *J. Clin. Ultrasound*, May-June 1982, 10, 227-232.

36. P. Breslau et al., "Effect of Carbon Dioxide on Flow Patterns in Normal Extracranial Arteries," *J. Surg. Res.* 32, 97-103 (1982).

37. W. Hass, et al., "Joint Study of Extracranial Occlusion—II. Arteriography, Techniques, Sites and Complications" *Jama* 203, 159-166 (1968).

38. D. Phillips et al., "Detection of Peripheral Vascular Disease Using the Duplex Scanner III," *Ultrasound Med. Biol.* 6, 205-218 (1980).

39. F. Greene, Jr., "A Microprocessor Based Pattern Recognition Approach to Diagnosing Atherosclerosis," Master's Thesis, University of Washington (1979).

40. S. Sheriff, "Mathematical Feature Extraction Applied to the Entire Doppler Shifted Frequency Signal Obtained from the Common Carotid Artery (Abstract), *Blood Flow Theory and Practice*, The Biol. Eng'g Soc., London (1980) 34-1, 34-4.

41. R. Rutherford et al., "The Use of Velocity Waveform Analysis in the Diagnosis of Carotid Artery Occlusive Disease," *Surgery* 695-702 (1977).

42. B. Kowalski, "Pattern Recognition in Chemical Research," *Computers in Chem. and Biochem. Res.*, Vol 2, Academic Press, N.Y., (1976).

43. R. Lerski et al., "Computer Analysis of Ultrasonic Signals in Diffuse Liver Disease," *Ultrasound Med. Biol.* 5, 341-350 (1979).

TECHNICAL FIELD

This invention relates to an automatic, objective, noninvasive method for interpreting the degree of stenosis (blockage) of a vessel from ultrasound Doppler shift data of blood flow in the vessel. More particularly, the invention relates to a computer based empirical method of statistical pattern recognition between the patient's data and a database of known, preclassified spectra to diagnose the degree of stenosis of the carotid arteries of a patient into categories of stenosis. The system uses an ultrasonic scanner, a real-time, fast Fourier Transform spectrum analyzer, and a dedicated digital computer to perform the analysis of data from the common and internal carotid arteries.

BACKGROUND ART

Detection and assessment of carotid arterial disease is important for the treatment of transient cerebral ischemic events and for the prevention of stroke. Arteriography, an expensive, invasive procedure, has a risk of morbidity and mortality which restricts its use to selected patients. Noninvasive, diagnostic ultrasound is being developed as an alternative to arteriography.

For carotid artery occlusive disease associated with blood flow abnormalities, as detected with Doppler ultrasound, irregular flow patterns proximal to the lesion area were studied by Keller (ref. 17), and were further quantified by Rutherford (ref. 41), who used hand-measured waveform parameters. Computer measured parameters obtained from the common carotid artery were used by Greene (ref. 39) and Sherriff (ref. 40).

To determine the extent of arterial disease from ultrasound Doppler shift data from the common and internal carotid arteries, the computer-assisted method of the present invention is used to recognize patterns in the spectral and temporal characteristics of the backscattered Doppler signal. This methodology, referred to as "statistical pattern recognition," has found application in disciplines ranging from chemical research (ref. 42) to the identification of liver abnormalities using diagnostic ultrasound (ref. 43). Such an approach is well suited to the problem of assessing vessel stenosis, where, while the precise nature of the physical processes involved are not well understood, the extent of disease can still be determined. The algorithms involved in the method of the present invention have produced diagnostically useful results with clinical data taken under realistic conditions. The processing involved extracts the Doppler shift data characteristic of the degree of stenosis from artifact created by vessel wall motion, sample volume movement, and system noise.

Traditionally, the diagnosis of aretery disease required invasive arteriography (contrast angiography). More recently, ultrasound scanning has led to the diagnosis of disease based upon displays of the Fourier Transform spectra as analyzed by a spectrum analyzer. Such reading is difficult. The recorded spectra (as shown, for example) in the Knox et al., article (Ref. 25)) are a continual broadening of the signal as the degree of stenosis increases. To read the spectra to quantify the degree of stenosis requires great skill and experience. To detect a slowly changing condition is almost impossible.

With the methodology of the present invention, however, the amplitude/frequency data of the discrete fast Fourier Transform is processed in the computer using pattern recognition algorithms. The method processes the data of the charted spectra by extracting useful pieces or predominant characteristics of the data. With the present system, the diagnosis is obtained objectively and automatically from the material data, thereby eliminating the need of great skill or experience in interpretation. A technician can arrive at a diagnosis immediately without the need for a radiologist to read the chart, with the consequent delay in the diagnosis. Visual interpretation of such features as the peak systolic frequency, the diastolic frequency, the amount of spectral broadening, or the overall shape of the waveforms makes it virtually impossible for even the most skilled radiologists to classify various stenoses objectively and to quantify which features are associated with each degree of stenosis. Pattern recognition of amplitude and frequency data offers a sophisticated statistical and analytic methodology that dissects the ultrasound Doppler spectra to extract the important diagnostic information automatically.

DISCLOSURE OF INVENTION

To diagnose automatically and objectively the degree of stenosis in a vessel, such as the carotid artery, an ultrasonic scanner creates a backscattered, pulsed Doppler signal from the vicinity of the centerstream flow of blood at several locations along the vessel near the dichrotic notch. This Doppler signal is analyzed for its Fourier Transform frequencies in a real-time, fast Fourier Transform spectrum analyzer. The frequency-analyzed spectra are further processed in a dedicated digital computer so that pattern recognition between an ensemble average of the patient's spectra and similar, preclassified, known spectra in a database can be performed to classify the patient's data into a category reflective of the degree of stenosis. The classification scheme is hierarchical, based upon training algorithms that weight measurements or "features" of the spectra. For efficiency of processing, the data is initially compressed to select meaningful portions or features from the complete Doppler signal. Compression involves creating the ensemble average, selecting a representative amplitude v. time spectrum or contour at a given frequency representative of the true Doppler signal, and broadening the representative spectrum with representative frequency/amplitude contours around the basic Doppler contour.

The averaging reduces the effect of outlying, apparently aberrant data points which can otherwise be a problem. If desired, the widths of the spectral broadenings may be scaled by dividing the measured width by the cosine of the Doppler angle (usually 60°). Scaling allows determination of the significance, if any, of the Doppler angle on the diagnosis. Also, spectral symmetry can be investigated.

The comparison of features is done with ARTHUR software for pattern recognition analysis using statistical methods that allow empirical diagnosis of the degree of stenosis.

BEST MODE FOR CARRYING OUT THE INVENTION

Figure 1:
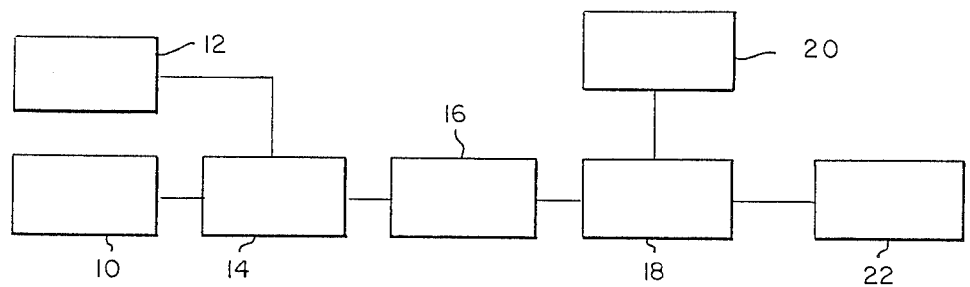
FIG. 1 is a schematic block diagram of the diagnosis system of the present invention.

A Duplex ultrasound scanner 10 is used to generate the patient database. The scanner 10 is a combined B-mode and pulsed Doppler scanner operating at 5 MHz, and provides a quadrature (bi-directional) Doppler signal. The common practice of filtering the Doppler signal in a high pass filter to remove wall noise can be eliminated. Patients with arterial disease often have Doppler signal components near 0 Hz, and these signals would be lost with a high pass. Signals near 0 Hz are prevalent in the period of late diastole or at the dichrotic notch, where flow reversal can sometimes be seen. The original Doppler electronics of the commercial scanner 10 had its wall filter 3 dB point altered from 1 kHz to 100 Hz so that flow information would not be lost in these cases. Thus, maximum sensitivity to arterial disease signals is gained by processing a wider bandwidth.

Usually the scanner 10 is a Mark V Duplex Scanner available from Advanced Technology Laboratories (ATL) in Bellevue, Washington (a division of Squibb). This scanner uses three fixed focus 5 MHz transducers imbedded in a rotating wheel, generating a two-dimensional sector image of soft tissue interfaces. The B-mode image is used to identify the vessel of interest, to visualize wall calcification, to recognize anatomical variations, to place the pulsed Doppler sample volume in the centerstream of the vessel, and, more importantly, to maintain a standard Doppler angle of incidence of about 60° between the Doppler beam and blood vessel axis. The B-mode image is stored electronically, while one of the transducers is used in the pulsed Doppler mode to monitor blood velocity within the sample volume. The orientation of the Doppler beam and the location of the sample volume are displayed on the B-mode image. The scan head usually uses 6 mm diameter transducers focused at a depth of 25 mm for data acquisition from the common and internal carotid arteries. The sample volume size for this transducer is about 3 $mm^3$ at this focal range, providing good resolution on the centerstream flow where wall disturbances have less effect.

While the system is usable for most major blood vessels, the present emphasis of research is into diagnosing the degree of stenosis in the carotid arteries, and this description will be limited to the carotid artery system. The anatomical sites from which velocity patterns are routinely recorded for carotid analysis are the low common carotid artery (l-CCA), the proximal internal carotid artery (p-ICA), and any sites along the bifurcation where high frequency signals are encountered. At each site, the angle between the Doppler beam and the longitudinal axis of the vessel is directly measured from the B-mode image. ECG timing information 12 is simultaneously obtained using a circuit which triggers from the R-wave. In addition to the voice of the technician (one channel), Doppler quadrature signals (two channels) along with the frequency modulated ECG R-wave signal (one channel) are automatically recorded on four-channel audiotape for off-line analysis. About 20-25 consecutive heart cycles are recorded on tape from each site. When disease is detected in the distal portion of the common carotid artery or in the proximal portion of the internal carotid artery (approximately the first two centimeters), the site of the maximum flow disturbance is used for analysis. This signal is identified by the technician either by a marked increase in Doppler frequencies or by the audible "roughness" of the signal. The tape recorded data are replayed through a real-time spectrum analyzer, and its digital output is generally written directly to disc.

In our experiments, data were recorded from the centerstream of four sites for each carotid system, providing a total of eight sites per subject: the proximal (approx. 3 cm proximal to the bulb) and distal (approx. 1 cm proximal to the bulb) regions of the common carotid artery, the internal carotid artery at the site of maximum audible disturbed flow, and the internal carotid site 1 to 2 cm distal to this point. The choice of two common carotid sites was based on experience which indicated that differences in flow behavior could be found at different points along this artery. Based upon further testing, it has been determined that data from the proximal common carotid artery and the proximal internal carotid artery are the only necessary data for the preferred system of the present invention.

Spectral decomposition of the directional Doppler signal is performed in the spectrum analyzer 14 employing a digital discrete fast Fourier Transform method (DFT). The spectrum analyser, such as a Custom Real Time FFT Spectrum Analyzer available from Honeywell, Inc. in Denver, Colorado, provides 400 spectra per second with a frequency resolution of 100 Hz. Every 2.5 msec, a new spectrum is generated, displaying 10 msec of Doppler frequencies. Adjacent spectra thus include 75% of old data and 25% of new data. The analysis range is 10 KHz with 7 KHz reserved for forward flow and 3 KHz for backward or reverse flow. The existence of frequency components beyond 7 KHz occurs regularly with severe stenoses, and can be inferred from the slope of the envelope of the discrete Fourier Transform (DFT) data that are available between 0 and 7 KHz. Usually, the slope of the DFT is smoothly varying and sufficiently close to zero between 0 and 7 KHz so that the higher frequency content of the Doppler data is obvious on the basis of extrapolation of the 0–7 KHz data.

A hardware and software interface with a PDP 11/34 or LSI 11/23 computer allows the transfer of the digitized spectral data and the ECG timing information from the spectrum analyzer directly onto disc storage 16. A data manager subroutine of the software is designed to allow the patient's background information (patient identification, age, symptoms, bruits, previous carotid surgery, etc.), the side and site of the signal, the Doppler angle, and other information as desired to be entered into the data file.

The spectral decomposition of the quadrature Doppler signal occurs in digital form. The conversion of the signal is to an accuracy of 8 bits, and is configured to output 100 bins of frequency information every 2.5 msec. The accuracy of the spectrum analyzer is ±5% in magnitude for each frequency bin.

The Doppler blood flow signal displays a statistical sample of the motions of individual blood cells within the sample volume. Each spectral pixel, 100 Hz wide and 10 milliseconds long, represents a portion of that statistical sample. The change and fluctuation of intensity from one pixel to the other is surprisingly large. The statistical variability in each pixel is reflected in the variability of two adjacent spectra, even through they share 75% of the data.

To reduce the variance of the estimate, a spectral averaging scheme is used. It has been designed to preserve temporal resolution within the cariac cycle while providing a better estimate of the true Doppler frequency distribution. The method generates a family of averaged spectra, each representing a different 10 millisecond portion of the cardiac cycle. Averaging will reinforce those characteristics of the waveform that are constant or periodic while reducing other nonperiodic or time variant characteristics (beat to beat variations, non-stationary system noise and other artifacts). Averaging avoids bias that would be involved in subjective selection of a "representative" heart beat.

Spectral averaging is usually done by inputting the signal data from disc into the dedicated digital computer 18 at the 40 kbyte/sec data rate of the spectrum analyzer or at whatever other data rate is suitable, summing the signals, and dividing by the total number of signals. ECG timing information is obtained using a hardware circuit which triggers off of the R-wave, while rejecting amplitude and baseline variations and accentuated P and T waves. The Doppler shift data, thus, are segmented into corresponding cardiac cycles based on the R-wave timing.

Since myocardial electromechanical delay is relatively constant from beat to beat, the R-wave is selected as the time reference to synchronize the averaging of data. To eliminate artifacts due to cardiac arrythmias, any signal is rejected if it has an R-R interval that either differs from the previous interval by more or less than about 110 msec or is longer than the previous interval by more than about 33%. Other factors could be used as a separation rule for arrythmias.

The rejected beats may be arrythmial (heart irregularities) or anomalous beats such as premature ventricular contractions. The 33% rule includes, however, all beats which are normal heart rate variations. Again, bias in the analysis is reduced, since an objective rule is used.

The spectral records from a plurality of otherwise consecutive, acceptable heart beats are summed to provide an ensemble average spectrum for the patient. The ensemble average is calculated according to the formula:

$$E(f,t) = \sum_{n=1}^{K} E(f,t,n)/K$$

wherein:
E is the DFT amplitude at f,t,n;
f is the frequency;
t is the time (measured in 280 2.5 msec intervals following the ECG R-wave);
n is the sequence number of the cardiac spectrum; and
K is the number of spectra in the ensemble average (usually 15–20).

Fifteen to twenty individual spectra provide a stable average representative of the patient's condition. If less than 15 spectra are averaged, improper diagnosis can result, since the variance of the average can be too large. If more than 20 spectra are used, little improvement is found and some reduction in diagnostic value may result. The spectra become irregular because of fatigue of the technician in moving the scanner, or because of changes in the patient caused by the length of the examination. Twenty spectra are preferred.

Consecutive, acceptable spectra are averaged to avoid introducing bias through the arbitrary selection of spectra.

An estimate of the true power spectrum of the Doppler signal, (obtained by performing a Discrete Fourier Transform (DFT)), is subject to statistical error. The behavior of this error can be studied analytically by deriving its variance. Oppenheim and Schafter have shown that for a Gaussian random process:

$$\begin{aligned}\text{Var}\,[\hat{P}(f)] &= P(f)[1 + (\sin 2fN)/(N \sin 2f)] \\ &= P(f)\left[1 + \frac{\sin(2fN)}{\operatorname{sinc}(2f)}\right]\end{aligned}$$

where:
$\hat{P}(f)$ = the estimated power spectral density (periodogram), as a function of frequency, f
$P(f)$ = the true (underlying) power spectral density from which the observed estimates $[\hat{P}(f)]$ are being generated
N = number of data points in the DFT
$\operatorname{sinc}(x) = \sin(x)/x$ The Doppler signal should be Gaussian since it is produced by a sufficiently large number of random scatterers (blood cells). Because:

$$\lim_{N\to\infty} \text{Var}\,[P(f)] = P(f),$$

the error in the estimate does not converge to zero as the number of samples, N, increases (i.e., this is not a "consistent" estimate). Improvement, however, can be obtained by averaging successive estimates. In particular, Welch has shown that:

$$\text{Var}\,[\hat{P}(f)] = P(f)/K, \text{ (for } N \text{ sufficiently large)}$$

where: K=number of spectral averages.

Because the variance of the estimate, at each frequency, is equal to the true power spectrum at that frequency if no averaging is done (K=1), the DFT can differ markedly from the true underlying spectrum unless an average is used. A variance of the nature found here means that the true spectra is between 0 and twice that of the estimate which is measured.

The variance reduction averages spectra from 20 successive acceptable heart cycles, at identical points in time with respect to each R-wave. The size of the resulting data file, even though 1/20 of the raw data, is such that the storage disc can still only hold data for about eleven patients. Further compression is necessary, and such compression will be explained.

The ARTHUR software system, which is available from the University of Washington, is used as a foundation of subroutines for performing pattern recognition. This package provides the necessary software for approaching the generalized problem of recognizing patterns in stochastic data, when little or nothing is known about the form of the underlying probability densities. A database management system is implemented to organize the large amounts of data involved.

The pattern recognition approach relies on the use of data representing known states of nature (e.g., disease) to "train" a classification scheme. This "training data base" is then used to develop a decision rule, which is used to classify unknown data.

The training database, available from the University of Washington and Washington Research Foundation, consists of data from diseased and normal arteries. Patients considered to have arterial disease were independently assessed by contrast arteriography (angiography), which provided an estimate of the percent diameter reduction based on the average of independent readings taken by two radiologists but read by only one. The estimate used was:

$$\% \text{ Stenosis} = 100 \times 1 - \frac{\text{Unoccluded vessel diameter}}{\text{Total vessel diameter}}$$

Diseased patients ranged in age from 38 to 82 years, with a median of 61 (mean=61.7). Normal data was obtained from subjects who were presumed to be disease free on the basis of being asymptomatic and free of bruits. Their ages ranged from 21 to 43 years, with a median age of 27 (mean=28.5). The training database includes compressed, ensemble average spectra of each known condition, and the complete ultrasound Doppler signal data is available for cross validation or expanded study, if necessary.

The training database probably will never be reassembled since contrast arteriography is not regularly prescribed due to its risk. With the ascendency of ultrasound and other noninvasive diagnostic techniques, doctors refuse to allow contrast arteriography, which imposes risks similar to surgery upon the patient.

Disease states identifiable within the Doppler data are considered to be categorical, rather than continuous. If categorical, the diagnostic approach: (1) recognizes that natural groupings may exist in the data (e.g., normal, diseased), (2) permits estimation of the probability of misclassification, and (3) reduces the problem of error in the individual arteriogram readings by looking for a natural clustering of spectra for a particular condition in the data rather than by looking for a predictable variation in a regular fashion as stenosis increases. Errors may arise in individual spectra from inherent uncertainties in the unoccluded vessel diameter, even with the contrast arteriography measurement. The estimates of stenosis are based on planar images of an irregular three-dimensional lesion within the vessel. A recent study indicates that disagreement rates between radiologists of 17.5% can occur when using the arteriogram to identify a disease state as 0, 1–9, 10–49, 50–99, or 100% stenosis or 12.5% when identifying a disease state as 0, 1–20, or 21–99% stenosis. These variations are reduced with a categorical pattern recognition methodology, which merely seeks clustering since major trends are recognizable even though fine details may be lost.

The patient's data are classified according to a heirarchical series of separate binary decisions under one of the following schemes:

---

A

For a vessel which is not fully occluded,
DECIDE Normal v. Diseased;
    If Diseased, THEN DECIDE greater v. less than 50% stenosis;
    If less than 50% stenosis, THEN DECIDE greater v. less than 20% stenosis.

B

For a vessel which is not fully occluded,
DECIDE Normal v. Diseased (partially occluded);
    If Diseased, then DECIDE greater v. less than 50% occluded;
        If less than 50% occluded, then DECIDE if greater or less than 35% occluded;
        If less than 35% occluded, then DECIDE if greater or less than 15% occluded

---

Further categorization may be achievable, if desired.

The initial decision must be whether the vessel is open or fully occluded (blocked), since forced misdiagnosis will occur if the vessel is occluded and exhibits no flow. The hierarchy for later decision presumes flow in the vessel and forces later decisions. The initial determination (open v. blocked) is made by observing a flow signal in the internal carotid artery as well as in the proximal common carotid artery. If flow is detected in the internal carotid, the computer diagnosis pattern recognition system can be used. If no flow is detected, the vessel is fully occluded, and the technician makes the diagnosis without the spectral pattern recognition.

When the averaged data are compressed, the essential information needed for successful pattern recognition analysis can be extracted. The "essential information" consists of location and scale estimators for the Doppler spectra, which are indicators of a frequency within the signal and the spread of the spectrum associated with that characteristic frequency.

To begin the data compression, one Doppler signal representative of the blood flow (and indicative of the degree of stenosis) must be found in the noise received with the backscattered signal. An algorithm to perform this function has been developed and tested on clinical data. The algorithm finds the mode (maximum amplitude) frequency of the Doppler signal, after using a rank order statistic to find the region of the spectrum containing the signal. The rank order statistic is resistant to high amplitude, narrow bandwidth noise (e.g., wall artifact). The maximum amplitude frequency for the spectral average determines the signal mode frequency for extracting the characteristic amplitude v. time contour signal from the 280 time bins of the ensemble average. That is, for each time interval in the cardiac cycle recorded in the Doppler shift data, the amplitude of the maximum amplitude frequency is used to define the mode signal contour by finding the amplitude of the signal at that frequency in each of the 280 time bins (pixels) across the spectrum.

The maximum amplitude frequency is determined by preparing a plot of amplitude v. frequency from the Doppler shift data. As such, the maximum amplitude and its corresponding frequency are easily extracted.

The scale or breadth of the Doppler shift flow signal is conveniently estimated for the characteristic contour by fitting contours at 3 db (the signal half-power points) and 9 db from the mode signal contour. The mode signal contour and spread contour estimates are improved using a running median filter in the calculation. This approach has proven to be insensitive to most cases of wall artifact, background noise, and quadrature channel cross-talk. Of course, other scaling or broadening techniques can be used.

Since late diastolic flow information is potentially valuable in the analysis, a method of obtaining this information from the ensemble average spectrum is needed. The method should be insensitive to the widely varying R-R intervals observed between different patients. By including 100 msec of data immediately preceding each acceptable R-wave spectrum in the ensemble average, late diastolic information can be easily included, however, in the compressed contours representative of the frequency and amplitude bandwidth of the complete Doppler shift data.

Figure 3:
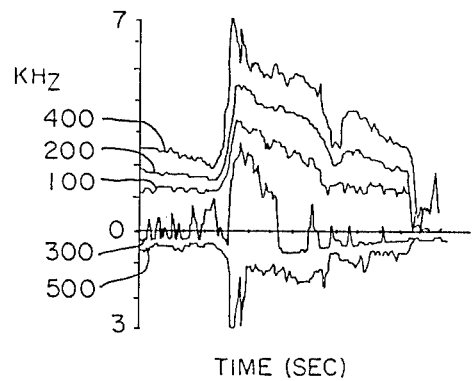
FIG. 3 is a representation of the compressed data in an ensemble average. This data is used in the pattern recognition system to determine the relative degree of stenosis.
Figure 2:
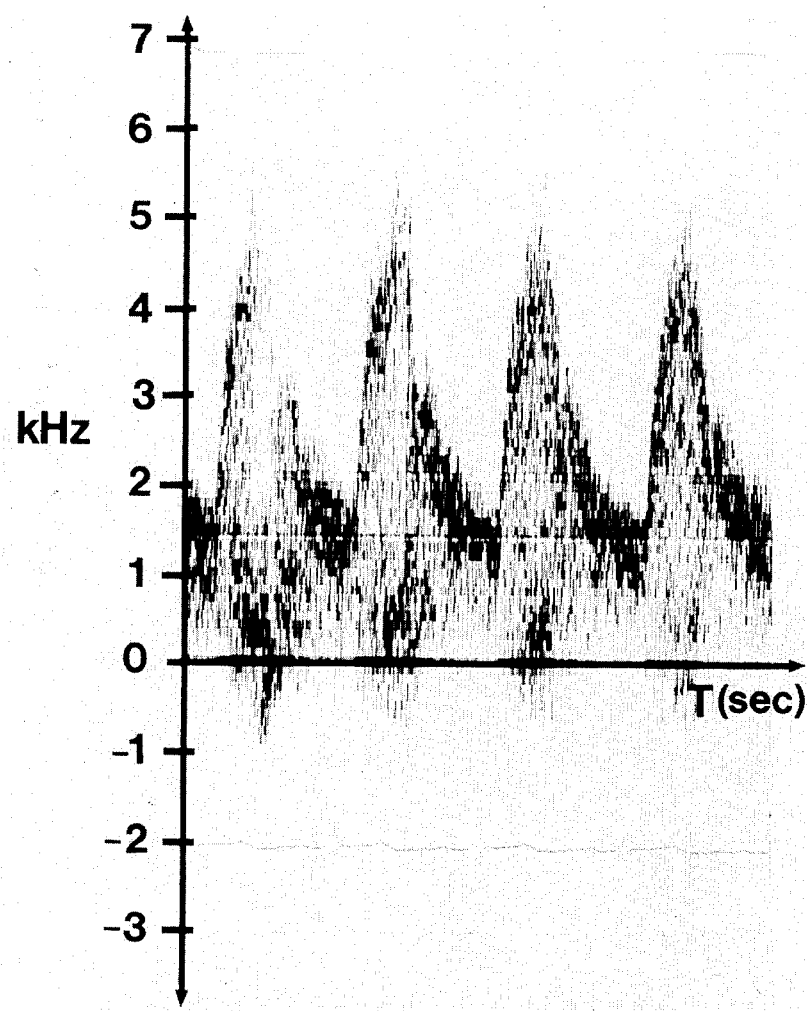
FIG. 2 is a schematic representation of a typical Doppler signal in an amplitude v. time plot.

The compressed data FIG. 3) comprises five contour lines showing Doppler amplitude v. time for each frequency. The central contour line 100 (FIG. 3) represents the mid-frequency or mode signal frequency best representative of the blood flow at the center stream of the vessel. The pair of lines or "scale contours" 200 or 300 immediately surrounding the mode signal contour 100 mark the 3 dB points, and the outermost pair 400 and 500 represent the 9 dB points with respect to the mode. These contours compress the data to 1400 bytes per site ([4 conturs+1 mode]×[280 time bins]=1400 bytes). A further data reduction of twenty to one is achieved Compressed data for several hundred patients can fit on one disc, which facilitates data analysis.

The pattern recognition scheme compares features of three general types: (1) those involving time relationships of the velocity waveform; (2) those involving the spectrum's width at preselected points along the heart cycle; and (3) those involving frequency decomposition of the estimated mean frequency waveform. The mean frequency waveform or mode contour line is analyzed in a windowed Discrete Fourier Transform to extract the principal Doppler frequency components between 1–20 Hz. Ninety-four features were initially identified as potential features for comparison, and are outlined in Table 1.

TABLE 1

Potentially Important Pattern Recognition Features
Some of these features were scaled or transformed using log or power functions to provide the features actually used in the discriminant equations.

I. Proximal Common Carotid Artery.
  (1) Area under mean flow waveform
  (2) Cos (Θ)
  (3) Sin (Θ)
  (4) Area under the systolic peak/cos (Θ) ±

TABLE 1-continued

Potentially Important Pattern Recognition Features
Some of these features were scaled or transformed using log or power functions to provide the features actually used in the discriminant equations.

15 msec bins
A. Mode frequency features
  (5) Late diastole (50 msec before the ECG R-wave)
  (6) Systolic Peak
  (7) First zero slope point after peak systole
  (8) Dichrotic notch
  (9) Decrease in frequency from peak systole to the first zero slope point after peak systole/cos (Θ)
B. Diastolic flow rate features
  (10) 125 msec after dichrotic notch/cos (Θ)
  (11) 50 msec prior to R-wave/cos (Θ)
  (12) Maximum amplitude frequency in Windowed Discrete Fourier Transform (WDFT) between harmonics 4 and 9
  (13) Maximum amplitude frequency in WDFT between harmonics 5 and 9
  (14) Maximum amplitude frequency in WDFT between harmonics 6 and 9
  (15) Pourcelot's ratio
  (16) Mode systolic frequency/mode early diastolic frequency
C. Feature reflecting the presence/absence of a "systolic window"
  (18) Max. lower 3 dB freq. between t = (systole − 30 msec) and t = (systole + 50 msec)
  (19) Max. lower 9 dB freq. between t = (systole − 30 msec) and t (systole + 50 msec).
D. Phase information features (unwrapped)
  (20) Phase of 2nd harmonic
  (21) Phase of 3rd harmonic
  (22) Phase of 4th harmonic
E. Features based on spectral broadening
  (for ± 3 dB and ± 9 dB contours, respectively)
  (23–26) Late diastolic
  (27–30) Systolic
  (31–34) First zero slope point after peak systole
  (35–38) 100 msec past systole
  (39–42) Systolic/cos (Θ)
  (43–46) 75 msec past systole/cos (Θ)
  (47–50) 100 msec past systole/cos (Θ)
II. Proximal Internal Carotid Features
  (1) Area under mean flow waveform
  (2) Cos Θ
  (3) Sin Θ
  (4) Area under the systolic peak/cos (Θ) ± 15 msec bins
A. Mode value features
  (5) Late diastole (50 msec before the EKG-R wave)
  (6) Systolic peak
B. Maximum features
  (7) Peak 3 dB frequency
  (8) Peak 9 dB frequency
  (9) Amount of deceleration following systole/cos (Θ)
  (10) Energy in maximum amplitude between harmonics 5 and 9
  (11) Frequency of minimum amplitude in WDFT from 2 to above maximum
  (12) Pourcelot's ratio = (Systolic − 1st zero slope/Mean), using mode waveform
  (13) Ratio = (Systolic − 1st zero slope)/systolic); using upper 9 dB contour waveform
  (14) Ratio = (systolic, using estimated mean waveform)/late diastolic, using upper 9 dB waveform
C. Features reflecting the presence/absence of a "systolic window"
  (15) Max lower 3 dB freq. between t = (systole − 30 msec) and t = (systole + 50 msec)
  (16) Max lower 9 dB freq. between t = (systole −

TABLE 1-continued

Potentially Important Pattern Recognition Features
Some of these features were scaled or transformed
using log or power functions to provide the features
actually used in the discriminant equations.

30 msec) and t = (systole + 50 msec)
D. Features based on spectral broadening
(for ± 3 dB and ± 9 dB contours, respectively)
(17–20) Late diastole (50 msec prior to R-wave)
(21–24) Systolic peak
(25–28) 50 msec past systolic peak
(29–32) 100 msec past systolic peak
(33–36) Systolic peak/cos (Θ)
(41–44) 100 msec past systolic peak/cos (Θ)

wherein $\theta$ = Doppler beam to vessel axis angle.

For features involving time relationships, the 5 contour ensemble average spectrum was further compressed to a single weighted average contour, with weights assigned according to the relative amplitudes of the contour in question, according to the formula:

$$f(t) = \{m(t) + 2[U_1(t) + L_1(t)] + b[U_2(t) + L_2(t)]\} / (1 + 2[a + b])$$

wherein
$m(t)$ = spectral mode at time t;
$U_1(t)$ = upper 3 dB frequency at time t;
$L_1(t)$ = lower 3 db frequency at time t;
$U_2(t)$ = upper 9 dB frequency at time t;
$L_2(t)$ = lower 9 dB frequency at time t;
$a = 10^{-3/20}$; and
$b = 10^{-9/20}$ The systolic peak and the first inflection of the systolic peak were located using the median smoothed first derivative of the maximum amplitude frequency (or mode) contour 100. The contour was smoothed according to the method of Mosteller and Tukey.

For features involving the width of the spectrum, the width was measured from the mode contour to the desired scale contour and was averaged for a ±12.5 msec (5 bins) window centered about the specified time.

Because the pattern recognition system weights the features linearly, it is important to non-linearly transform the "raw features" (those chosen from Table 1) in an effort to maximize their effectiveness in the linear discriminant equations. Therefore, exponential and power functions of the basic features were calculated and plotted to test for linearity. For convenience and simplicity with the present invention, stepwise linear regression was used to select features, and has proven to be adequate insofar as the selected features contain unique rather than redundant information.

The features were re-scaled for zero mean and unit variance. By stepwise discriminant analysis of the 94 features, classification of the known vessels in the database (training set) was made using the best combination of 5 features selected from the 94 for each hierarchical decision. Thereafter, only these 5 features are used to diagnose the degree of stenosis from a patient's ensemble average. The five features used for each hierarchical decision (i.e., normal v. diseased; greater than 50% stenosis v. less than 50% stenosis, etc.) are selected separately by the discriminant analysis from all 94, original features against the data of known arterial conditions. Of course, other features or additional features, selected in different ways might be used. Five features are preferred because they appear to provide a high degree of accuracy. An acceptable balance is achieved so that each feature is significant, while relatively meaningless or redundant features are not introduced. Although the system could be biased by the selection of features by this discriminant analysis method, empirical evidence shows that this format is a highly accurate, automatic, and objective tool for correctly diagnosing carotid artery stenosis.

The preferred features selected for each decision are:

TABLE II

1. Normal v. Diseased
   - ln (the value of the early diastolic mean flow in the common carotid artery/cos Θ)
   - −[post systolic change in frequency/cos Θ]$^4$ at common carotid artery
   - ln (mode of DFT waveform) at the internal carotid artery
   - (lower 9 dB point of the waveform)$^4$ at the internal carotid artery
   - ln (late diastolic mean flow/cos Θ) at the common carotid artery
2. Greater than 50% stenosis v. less than 50% stenosis
   - [peak 9 dB frequency]$^2$ at the internal carotid artery
   - [maximum lower 9 dB frequency between ± 50 msec of the systolic peak]$^4$ at the internal carotid artery
   - −[post systolic change in frequency/cos Θ] at the internal carotid artery
   - ln [first minimum in DFT waveform] at the internal carotid artery
   - [Upper 9 dB width 50 msec after systole]$^4$ at the internal carotid artery
3. Greater than 35% stenosis v. less than 35% stenosis
   - peak 9 dB frequency at internal carotid artery
   - ln [frequency 125 msec before the dichrotic notch of the common carotid artery]
   - ln [change of systolic frequency at the internal carotid artery/cos Θ]
   - ln [lower 9 dB DFT waveform] at the internal carotid artery
4. Greater than 15% stenosis v. less than 15% stenosis
   - ln [area under the peak for period ± 37.5 msec around systole] at the common carotid artery
   - ln [peak 9 dB frequency] at the internal carotid artery
   - peak 9 dB frequency at the internal carotid artery
   - upper 9 dB width 125 msec after diastole at the common carotid artery
   - ln [lower 3 dB width 125 msec after diastole] at the internal carotid artery
5. Greater than 20% stenosis v. less than 20% stenosis
   - ln [area under the peak for period ± 35.5 msec around systole] at the common carotid artery
   - ln [peak 9 dB frequency] at the common carotid artery
   - peak 9 dB frequency at the internal carotid artery
   - lower 9 dB width 100 msec after systole at the common carotid artery
   - ln [mode of DFT waveform] at the common carotid artery This 20% stenosis determination apparently is accurate enough using a redundant test regarding the peak 9 dB frequency.

If it is desirable to determine whether the vessel stenosis is greater v. less than 80%, the preferred features are:

6. Greater than 80% stenosis v. less than 80% stenosis
   - ln [upper 9 dB width at systole] at the internal carotid artery
   - ln [maximum 3 dB frequency between ± 50 msec of the systolic peak] at the internal carotid artery
   - ln [first moment of the systolic peak/upper 9 dB frequency 125 msec after diastole] at the common carotid artery
   - ln [mode of DFT waveform] at the internal carotid artery A hyperplane solution method of pattern recognition based on linear regression analysis in the ARTHUR software is used. The preferred method, according to Pietrantonio and Jurs (commonly known as Pjurs) iteratively minimizes the function:

$$\left[ Y - \tanh\left( W_o + \sum_{i=i}^{K} W_i X_i \right) \right]$$

where:

Y
  = +1 m if data are known to be in category 2
  = −1, if data are known to be in category 1
Y = predicted category
K = number of features
$W_i$ = weight of feature
$X_i$ = measured value of feature i
$W_o$ = constant To assure a higher degree of accuracy, cross validation is used. Cross validation involves splitting the training database into two subsets for each category of stenosis being tested, training the classifier based upon one subset, and, then, retesting the decision rule of the classifier by running the classifier on the second subset of data.

A randomly selected number of the compressed spectra data, comprising about 50% of the database, was selected at each iteration of the cross validation process in a "half-sample plus complement" cross validation scheme. The subsets were restricted to avoid overestimating the true accuracy of the classification rule, as might otherwise occur if the selected subset were a larger portion of the database.

The estimated accuracy of the classifier achieved with this cross validation method is the mean percent correct in the test sets. At each decision in the hierarchy of format A, the percent correct was 97% for the first decision (normal v. diseased), 95% for the second decision (greater v. less than 50%), and 84.3% for the third decision (greater v. less than 20%). The sum of the five weighted features were used to determine the discriminant score for each decision.

The classification scheme currently used goes through four separate binary decisions in a hierarchical order, namely:

(1) DECIDE normal vs. diseased;
(2) If diseased, THEN DECIDE greater v. less than 50% stenosis;
(3) If less than 50% stenosis, THEN DECIDE greater v. less than 35% stenosis; and
(4) If less than 35% stenosis, then DECIDE greater v. less than 15% stenosis.

In this way, six categories are established, namely: (1) undiseased, (2) 0–15% stenosis, (3) 16–35% stenosis, (4) 36–50% stenosis, (5) over 50% stenosis, and (6) fully occluded (100% stenosis). The categories are arbitrary for the intermediate splits, and were selected on the basis of the extent of the data from arteriographs, and the desire to obtain relatively high resolution of the progression of disease. Other break points could be established such as the 0–20, 20–50, and greater than 50% format already discussed. The split between greater or less than 15% stenosis gives an early warning of dangerous progression of the disease. The radiologist made the first diagnostic assessment at 15% occluded or less, so this point is the first step of disease progression that can be achieved with this database.

The ultimate test of system performance of the classifier, however, is to evaluate data from patients with known stenosis, but whose data was not used in the design of the classifier. The test patients analyzed to test the classifier consisted of nine volunteers, who presumably were normal, and 95 patients with extracranial arterial disease assessed angiophyically. In the total group, there were 170 sides suitable for study. The remaining 38 sides were not included in the analysis for the following reasons: (1) 16 sides had occlusion of the internal carotid artery; (2) 12 sides had an endarterectomy performed before the ultrasonic study; and (3) 10 sides were lost because of mechanical failure of the data recording system.

A double blind test was developed wherein the radiologist, who read the biplane contrast arteriograms, was unaware of the diagnosis provided by the computer analysis and the Doppler technician was unaware of the radiologist's diagnosis.

The Kappa statistic as used by Cohen, Fleiss, and Langlois was calculated to measure the degree of agreement between two raters who evaluated the database independently. Accounting for chance in the diagnosis or decision, the formula becomes:

$$\text{Kappa} = (P_o - P_e)/(1 - P_e)$$

where $P_o$ is the observed probability of agreement and $P_e$ is the agreement that would occur on the basis of chance alone. The quantity $1 - P_e$ measures the degree of agreement attainable over and above that which would be predicted merely by chance. The degree of agreement actually attained in excess of chance is $P_o - P_e$. If the observed agreement is greater than or equal to chance agreement, Kappa will be greater than or equal to zero, with a maximum value of +1 for a perfect agreement. Similarly, if the observed agreement is less than chance agreement, the value of Kappa will be negative. For purposes of making this calculation, it was assumed that the sample size was large. Based upon the empirical results, this assumption seems to be acceptable.

The agreement between the computer results and angiography was 96.5% (164/170) for the normal vs. diseased decision, 93% (158/170) for the greater or less than 50% decision and 93% (158/170) for the greater or less than 20% decision. Of the 29 normal sides, 27 (93%) were correctly classified. The other two sides were classified in the 1–20% category and both were form the presumed normals (age 27 and 34), who actually had never had contrast angiography performed. Therefore, they might have actually had minor stenosis.

Of the 54 sides in the 10–20% stenosis category, 44 (81.5%) were correctly classified. Of the remaining ten sides, four were classified as normal, and six in the 21–50% category. Of the 37 sides in the 21–50% category, 29 (78%) were correctly classified. Of the remaining eight sides, five were misclassified in the 1–20% caterogy, and three in the 51–99% category (all three were diagnosed as a 50% diameter reduction by the angiography). Of the 50 sides in the 51–99% category, 41 (82%) were correctly classified. Of the remaining nine sides, one was misclassified in the 1–20% category, and eight in the 21–50% category.

The overall accuracy of the computer classification by category was 83% (141/170). The sensitivity of the method or ability to recognize the presence of disease was 97% (137/141) and the specificity 93% (27/29). The degree of agreement between the pattern recognition and angiography, as measured by the Kappa statistic, was: K=0.769±0.039 (Standard Error).

Sixteen sides, occluded by angiography, were omitted. The diagnosis of an occlusion was recognized by the absence of signal in the internal carotid artery, thus precluding computer analysis. In no instance was a signal submitted to computer analysis when the artery was called occluded by angiography, since the classifier was forced to find some flow in the vessel. No vessel was omitted from computer analysis, however, merely because occlusion was diagnosed on the duplex scan but not with angiography.

The decision of occluded (completely blocked) v. open can be added to the decisional hierarchy, if desired, by having the computer search for a Doppler shift signal in the internal carotid artery. In this way, all decisions would be made by the computer and no judgment would be left to the technician.

Because the Doppler shift frequency is directly proportional to the cosine of the Doppler angle relative to the flow stream, calculation of flow velocity can only be made when this Doppler angle is known. Wall calcification and anatomical variations (both known to alter the flow signal) are easily assessed by B-mode imaging.

A pulsed Doppler unit, through range gating, permits flow interrogation at specific depths along the beam axis. Previous clinical experience has shown that a scanner with a focal point at or near two centimeters beneath the surface of the skin is appropriate for studying the carotid arteries. Also, a small sample volume relative to the diameter of the vessel allows sampling of flow from a centerstream site, allowing avoidance of the velocity gradients near the vessel wall. The scanner had a focal length of 25 mm and a sample volume size of 3 $mm^3$ at its focal point to provide the desired resolution. The image of the scanner established anatomic landmarks used for standardizatio of sampling sites. These landmarks were essential for comparing conditions of different patients or for comparing sequential studies on the same patient.

Since no features were selected in the preferred classification process from the distal internal carotid arteries or from the high common carotid artery (which is prone to misclassification, if selected), the only data which actually need be collected from each patient can be reduced to Doppler shift data from the low common carotid artery (about 2 cm above the divide) and from the proximal internal carotid artery, rather than data from the four sites we used in our experiments. Thus, the data can be compressed even further.

Although it has several advantages over other schemes, the compressed data format we use may not be the optimal one. The scheme permits: (1) a sensitive assessment of rapid changes occurring in the Doppler signal with time; (2) an easy interpretation of the spectrum; (3) an adequate representation of the usual asymmetry of the signal spectral density; (4) a reliable tracking of the signal in the presence of both narrow and wideband noise of varying intensity; (5) a data reduction sufficient to facilitate storage, handling and analysis; and (6) adequate data for extraction and identification of informative features necessary for good partition of the state of disease.

A typical waveform for blood flow in the common carotid artery proximal to a normal internal carotid artery is characterized by a high, sharp, narrow systolic peak with little or no notching in the decelerating phase and a high peak diastolic flow. A typical waveform for blood flow in the common carotid artery proximal to a minimally diseased internal carotid artery reveals a much lower, broader, and "rounded" systolic peak, a prominent notch in the early decelerating phase, and a more dampened diastolic flow. These general differences can be categorically analyzed, assessed, and classified with the compressed data and pattern recognition format of the present invention.

The first decision (normal vs. diseased) and the second (greater vs. less than 50%) appear to be important for making a decision on management of the patient. The reasons for defining further categories of stenosis, however, are less obvious. A decision point at the first level (15 or 20% occluded) was initially based on: (1) the need to grade disease further than merely greater or less than 50% stenosis to allow assessment of progression of disease; (2) evidence that the agreement between radiologists reading the same arteriographs is higher at the 20% level than at the 10% level; and (3) a natural minimum occurred in the distribution of the training database at 20%. Increasing the size of the data base may permit further gradation in the 51-99% category. Although further discrimination in the 51-99% category is possible, finer tuning of the program to distinguish changes of greater or less than about 15% appears unrealistic, considering the lack of precision in the interpretation of actual arteriograms.

In actual experiments we have tried to assess the importance of the technician in obtaining a correct diagnosis for the degree of stenosis. Our tests involve the taking of ultrasound Doppler data on the same patient at three different hospitals and analyzing the data [taken by different technicians] with the digital computer in the pattern recognition scheme described in this invention. We have found that in about 90% of the cases, the computer diagnoses are the same as or within one category of one another. That is, if we classify the degree of stenosis as 36-50% occluded, 90% of the time, a technician at another hospital in the test will find the degree of stenosis to be 15-35%, 36-50%, or greater than 50% (within one category). Thus, the system has proven successful as a noninvasive tool to identify disease and at least crudely to specify the degree of stenosis. We are seeking further refinements in the method to improve the reproducibility, and to remove bias introduced during data acquisition.

The classification scheme of the present invention is discrete and ignores possible conflicts faced at each decision. It forces a decision for one category. For example, an artery classified as normal in the first decision could still be classified as having more than 50% stenosis at the second decision step. According to the actual training set and prospective test set, the chance that an artery would have more than 20% occlusion or stenosis while being called normal in the first decision is only 2.5%. Similarly, no vessels having less than 20% stenosis have been classified as having more than 50% stenosis with the actual classifier. The classifier misses generally only by one category.

Misclassification most often results from very tight stenoses in patients whose data was characterized by a quasi-steady, nonpulsatile type of flow pattern. This type of flow pattern is poorly represented in the training database. As more of this type of data becomes available, the classification algorithm will undoubtedly be modified, since the training database will have a better base on which to make classification decisions. Flow patterns of this type will be added to the database to improve the database and the decision making.

The level of agreement between the computer diagnosis and angiography, as measured by the Kappa statistic equals 0.77+0.04 (Standard Error). This level of agreement compares favorably with the level of agreement that can be reached by different radiologists reading the same arteriograms, so great promise is shown for the system.

We will continue to attempt to improve the feature definition and feature selection. To distinguish and grade further within the 51-99% category, a more adequate surveillance of the progression of arterial disease will be necessary during long-term follow-up studies. To determine with precision the site of sampling within the vessel and to reduce the possible variability involved in the placement of the pulsed Doppler sample volume, the possibilities of using a three-dimensional position locator will also be explored. Expected to permit sampling of flow within 1 mm of a previously sampled site, this method could find a particular application when serial duplex studies are performed.

Selected Portions of the Analytical Software

The following software is the preferred coding presently being used to do the required calculations to analyze features at the common and internal carotid artery sites and to identify important landmarks in the data, such as systole, relative minima, or relative maxima. The comments in the software and the conventional FORTRAN coding will illustrate to one of ordinary skill in this art the calculation format used for locating features.

```
        .TITLE  MAXAMR
        .ENABL  LC
        .GLOBL  MAXAMR
        .GLOBL  SRKMBA, PRCENT, MEDIAN, SWABTS, GTBYT
        .GLOBL  SRTMIF

; MAXAMR --
;       FORTRAN callable subroutine to return a resistant estimate
;       of the mode (tends to ignore outliers in a non-linear
;       fashion).  It functions as follows:
;       1) Sort the spectrum on the input data, after putting the
;          original order in the upper byte of each word.
;       2) Take the upper "NROBUS" elements, or until the "NOISE" level
;          is reached, or until "LIMIT" % of the overall maximum is reached
;          and ...
;       3) ... return the median of this bunch as the mode.

; On Entry --
;       The input file is assumed to be positioned at the beginning
; of the spectrum (or whatever) to be scrutinized.
;       2(R5) is address of the array having the spectrum.
;       @4(R5) is the number of elements (words) in the array.
;       @6(R5) is the "amount of robustness" desired.  It will
; determine the maximum number of data points to consider in
; making the estimate.

; On Exit --
;       The integer estimate is returned @8.(R5).
;       The input file is advanced to the byte following the
; array just analyzed.

; Assembler constants.
LIMIT   = 50.
NOISE   = 5.

MAXAMR:
; Force reasonable values for input parameters.
        TST     @4(R5)
        BGE     1$
        CLR     @4(R5)
1$:
        TST     @6(R5)
        BGE     2$
        CLR     @6(R5)
2$:
;       "R" value to R4, where it will stay.
        MOV     @6(R5),R4

; Put frequency indeces in the upper bytes of the input array.
        MOV     2(R5),R1                ;R1:= address of array.
        MOV     @4(R5),R2               ;R2:= no. of elements in array.
        CLR     R3                      ;R3:= freq. index.

SETKY:
        MOVB    (R1),R0                 ;Next datum to R0.
        SWAB    R0                      ;Put upper byte in position.
        BIS     R3,R0                   ;Mask in the freq. index.
        SWAB    R0                      ;Restore order.
        INC     R3                      ;Next freq.
        MOV     R0,(R1)+                ;Store result in the array.
        SOB     R2,SETKY                ;Loop until done.
        MOV     R1,-(SP)                ;Save the end point.
```

```
; Sort the array from smallest to largest.
        MOV     2(R5),R1
        MOV     @4(R5),R2
        CALL    SRKMBA ; Compute the cutoff amplitude.
        MOV     (SP),R2         ;Restore end of array.
        DEC     R2
        MOVB    -11.(R2),R1     ;R1:= maximum amplitude.
        MOV     #NOISE,R3       ;R3:= Level below which data is noise.
        MOV     #LIMIT,R0
        CALL    PRCENT          ;R0:= threshold amplitude.

; Descend through the list.
        MOV     -1(R2),R1
        MOVB    R1,R2
        ASH     #-2,R2          ;R2:= Max. amp/8
        ADD     R2,R4           ;Increase "R" by (Max amp)/8.
        MOV     R4,R2           ;R2:= no. of points to consider.
        MOV     (SP)+,R1        ;Start at maximum.

DESCND: TST     -(R1)
        CMPB    (R1),R3         ;Below noise ?
        BLE     ESTIMA          ;Yes.
        CMPB    (R1),R0         ;Below threshold ?
        BLE     ESTIMA          ;Yes.
        SOB     R2,DESCND ; Compute the estimate. R1 addresses the point where the descent
; stopped. R4 +1 -R2 gives the no. of points in the estimate.
ESTIMA: SUB     R4,R2
        NEG     R2              ;R2:= no. of points in the estimate.
        INC     R2              ;Make sure there's at least one.
        CALL    SWABTS          ;Swap all the byte pairs.

; Sort according to frequency.
        CALL    SRKMBA

; Return the median.
        CALL    MEDIAN
;       BIC     #177400,R0
        MOVB    R0,R0
        MOV     R0,@8.(R5)

RETURN

.END
        .TITLE  LIMITS
        .ENABL  LC
        .GLOBL  LIMITS
        .GLOBL  SRKMBA,MEDIAN,SWABTS,WINEST

; LIMITS --
;       Computes a robust estimate of the high and low contours
; of a spectrum about the location point.

; On Entry --
;       @2(R5)= Location estimator.
;       @4(R5)= Threshold or contour level.
;       6(R5)=  Addresses the integer array with the spectrum having
;               frequency indeces in the upper bytes of each element.
;       @8(R5)= No. of elements in the spectrum array.
;       @10(R5)= Robustness.
```

```
; On Exit --
;       @12(R5)= Lower limit.
;       @14(R5)= Upper limit.

; Assembler constants.
NOISE   = 1.

LIMITS:
; Put the threshold in R3.
        MOV     @4(R5),R3
        CMP     R3,#NOISE               ;Threshold into noise margin ?
        BGE     1$                      ;No.
        MOV     #NOISE,R3               ;Yes, up the threshold.
1$:

; Compute address of location point.
        MOVB    @2(R5),R1
        ASL     R1
        ADD     6(R5),R1                ;Convert to byte count.
        MOV     R1,R2                   ;R1 & R2 both address location point.

; Search from location point downward to find low limit.
        MOVB    @2(R5),R4
        BEQ     LOWDNE
        TST     (R1)+
        ADD     #2,R4                   ;R4:= Distance to minus infinity.

LOWSEA:
        DEC     R4
        BLT     LOWDNE                  ;Test for end of buffer.
        DEC     R1
        CMPB    -(R1),R3
        BGE     LOWSEA LOWFND:
;       Check for consistency in next point.
        MOV     R1,R0
        DEC     R0
        CMPB    -(R0),R3                ;Next point < threshold ?
        BGE     LOWSEA                  ;No, keep searching.

LOWDNE:
; Search from location point upward to find high limit.
        MOV     @8.(R5),R4
        MOVB    @2(R5),R0
        SUB     R0,R4
        SUB     #2,R4                   ;R4:= Distance to plus infinity.
        BEQ     HIDNE
        TST     -(R2)

HISEA:
        DEC     R4
        BLT     HIDNE                   ;Test for end of buffer.
        TST     (R2)+                   ;Advance index ptr. to next word.
        CMPB    (R2),R3                 ;Below threshold ?
        BGE     HISEA                   ;No, check the next.

HIFND:
;       Check for consistency in next point.
        DEC     R4
        BLT     HIDNE                   ;Test for end of buffer.
        TST     (R2)+                   ;Advance index ptr. to next word.
        CMPB    @R2,R3                  ;Next point < threshold ?
        BGE     HISEA                   ;No, keep searching.
        TST     -(R2)                   ;Yes, correct for extra increment.
```

HIDNE:

; Convert R1 & R2 to index values.
```
        SUB     6(R5),R2
        SUB     6(R5),R1
```

; Return low & high limits.
```
        ASR     R1              ;Convert from byte to ...
        ASR     R2              ;... element count.
        MOV     R1,@12.(R5)
        MOV     R2,@14.(R5)

RETURN

.END

SUBROUTINE MARKS(BUFF,NPTS,NDELX,NX,NY,XSCALE,YSCALE,
     &   N1MAX1,N1MIN1,N1ZRO1,R1ARE1,NSYSTO,R1ARE2)
        BYTE BUFF(1)

C       Computes some interesting landmark information
C       from the sequence in "BUFF" which is assumed to
C       have a first derivative function in it.

C       Find maximum acceleration point in the systolic region.
        CALL EXTBYT(BUFF(50),120,N1MIN1,N1MAX1)
        N1MIN1= N1MIN1+50
        N1MAX1= N1MAX1+50

C       Find the supposed systolic peak.  This is defined to be the
C       first near-zero slope point following N1MAX1.
        DO 400,NSYSTO=N1MAX1,N1MIN1
          IF ( (BUFF(NSYSTO) .LE. BUFF(N1MIN1)+1)
     &    .OR. (BUFF(NSYSTO) .LT. 1) ) GO TO 500
400     CONTINUE
500     CONTINUE C       Find other extrema now that NSYSTO is defined.
        NSEARC= NSYSTO+10
        CALL EXTBYT(BUFF(NSEARC),65,N1MIN1,N1MAX1)
        N1MIN1= N1MIN1+NSEARC
        N1MAX1= N1MAX1+NSEARC CALL EXTBYT(BUFF((NPTS/2)+1),NPTS/2,N1MIN2,N1MAX2)
        N1MIN2= N1MIN2+NPTS/2
        N1MAX2= N1MAX2+NPTS/2

C       Find the first zero slope point after the max decceleration
C       point (N1MIN1), which is hopefully the first zero slope
C       point following systole.
        DO 600,N1ZRO1=N1MIN1,200
          IF (BUFF(N1ZRO1) .GT. -1) GO TO 700
600     CONTINUE
700     CONTINUE C       Compute the area under the post systolic decelleration curve
C       at the point of greatest decelleration.
        R1ARE1=0
        R1ARE2=0
        DO 300,I=N1MIN1-10,N1MIN1+10
          II=BUFF(I)
          IF(II .LT. 0) R1ARE2= R1ARE2 + II
300       R1ARE1=R1ARE1+BUFF(I)
        R1ARE1= R1ARE1/FLOAT(NDELX)
        R1ARE2= R1ARE2/FLOAT(NDELX)
```

```
C         Write bars out to the plot so people can see what happened.
          CALL BRAKIT(NX,NY,N1MIN1,N1MAX1,90,XSCALE,YSCALE)
          CALL BRAKIT(NX,NY,NSYSTO,N1ZRO1,100,XSCALE,YSCALE)

END
          SUBROUTINE BFEATU(LOCBUF,SCLBUF,
     &       NPTS,YSCALE,NXO,NYO,CBUFF1,CBUFF2,NROBUS,NCYCMX,PATNAM)
          COMMON /MARKS/NOMIN1,NOMAX1,NOMIN2,NOMAX2,N1MIN1,N1MAX1,
     &       N1MIN2,N1MAX2,NSYSTO,N1ZRO1
          COMMON /PARAMS/AREA,COSANG(3),SINANG(3),
     &       ROVAL1,ROVAL2,ROARE1,ROARE2,
     &       R1VAL1,R1VAL2,R1ARE1,R1ARE2,
     &       RMVAL1,RMVAL2,RMARE1,RMARE2,
     &       RPVAL1,RPVAL2,RPARE1,RPARE2,
     &       SLOPE
          COMMON /ARRAYS/SCR1,SCR2,SCR3,RTIME,RMAG,RPHASE

VIRTUAL CBUFF1(1),CBUFF2(1)
          COMPLEX CBUFF1,CBUFF2,CTEMP
          REAL RTIME(512),RMAG(512),RPHASE(512),FEATS(1)
          BYTE PATNAM(1)
          BYTE LOCBUF(1),SCLBUF(NPTS,1)
          BYTE SCR1(512),SCR2(512),SCR3(512),NOTCHS(2)
          PI2= 3.14159265*2
          NPTP2= 512
          XSCALE= YSCALE/3.

C         Copy location data to scratch 1, real, and complex buffers.
          CALL STCOPY(LOCBUF,SCR1,NPTS)

C         Force effective end of data to occur at t= .5 sec.
          CALL INIBYT(LOCBUF(240),41,LOCBUF(240))
          CALL INIBYT(SCLBUF(240,1),41,SCLBUF(240,1))
          CALL INIBYT(SCLBUF(240,2),41,SCLBUF(240,2))
          CALL INIBYT(SCLBUF(240,3),41,SCLBUF(240,3))
          CALL INIBYT(SCLBUF(240,4),41,SCLBUF(240,4))

C         Subtract off the DC offset in the input data.
          CALL ADDBYT(SCR1,NPTS,-30)
          CALL ADDBYT(LOCBUF,NPTS,-30)
          DO 100,I=1,4
100          CALL ADDBYT(SCLBUF(1,I),NPTS,-30)

C         Remove the ECG trigger spike.
          SCR1(41)= SCR1(40)
          LOCBUF(41)= LOCBUF(40)
          DO 110,I=1,4
110          SCLBUF(41,I)= SCLBUF(40,I)

CALL DOTIME(LOCBUF,SCLBUF,NPTS,RTIME,NPTP2,AREA,PATNAM)
          IF (AREA .GT. 0.0) GO TO 120
           PRINT 111,(PATNAM(I),I=1,8)
111        FORMAT(' BFEATU-W-',8A1,' has zero energy')
           GO TO 5000
120       CONTINUE
C         Plot the location data.
          CALL PLTRE1(NXO,NYO,0,IFIX(30*YSCALE),
     &       XSCALE,YSCALE,RTIME,280,NROBUS,NCYCMX,PATNAM)

C         Initialize plotting coordinates.
          NXLO= NXO+NPTS +40
          NYLO= NYO- 30*YSCALE

CALL SCAREA(RTIME,512,1./AREA)
          CALL REACOM(RTIME,NPTP2,CBUFF1)
```

```
C       Find land marks in the velocity waveform.
C       (Use "SCR1" data for extrema since it has +.6 sec data intact).
        CALL EXTBYT(SCR1, (NPTS/2)+30,NOMIN1,NOMAX1)
        CALL EXTBYT(SCR1( (NPTS/2)+1 ),NPTS/2,NOMIN2,NOMAX2)
        NOMIN2= NOMIN2+ NPTS/2
        NOMAX2= NOMAX2+ NPTS/2
        CALL BRAKIT(NXO,NYO,(NOMAX1-1),(NOMIN2-1),35,XSCALE,YSCALE)

C       Compute first derivative and leave in scratch 3.
        NDELX= 9 ! Set delta X.
        CALL DERIV(LOCBUF,NPTS,NDELX,SCR2)
        CALL SMOOTH(SCR2,NPTS,4,SCR3)
        CALL MARKS(SCR3,NPTS,NDELX,NXLO,NYLO,1.,YSCALE,
       &  N1MAX1,N1MIN1,N1ZRO1,R1ARE1,NSYSTO,R1ARE2)
        CALL BRAKIT(NXO,NYO,NSYSTO,N1ZRO1,40,XSCALE,YSCALE)
        CALL SCABYT(SCR3,NPTS,2.5)
        CALL ADDBYT(SCR3,NPTS,50)
        CALL PLTBYT(SCR3,NPTS,NXLO,NYLO,1.,YSCALE)

NXFIL= NXO
        NYFIL= NYO-100*YSCALE-20

C       Compute the DFT and display the magnitude.
        CALL HAMEND(CBUFF1,NPTP2)
        CALL FFTFOR(NPTS,CBUFF1)

C           Phase to "RPHASE".
        DO 200,I=1,NPTP2
200        RPHASE(I)= AIMAG( CLOG( 1.0E-6+CBUFF1(I) ) )
C       Unwrap the phase.
        DO 400,I=1,511
           NDIFF= ( ABS(RPHASE(I+1) - RPHASE(I))/PI2 ) + .5
           IF ( RPHASE(I+1) .LT. RPHASE(I) ) NDIFF= -NDIFF
400        RPHASE(I+1)= RPHASE(I+1) - PI2*NDIFF
        SLOPE= -2*RPHASE( (NPTP2/2)+1 )
        DO 450,I=1,NPTP2
450        RPHASE(I)= RPHASE(I) + SLOPE*(I-1)/NPTP2
C       CALL REAREA(RPHASE,NPTP2,RMAG)
C       CALL EXTREA(RPHASE,NPTP2,RMIN,RMAX)
C       CALL SCAREA(RPHASE,NPTP2,50./(AMAX1(ABS(RMAX),ABS(RMIN))) )
C       CALL ADDREA(RPHASE,NPTP2,50.)
C       NXLO= NXLO+NPTS +40
C       CALL PLTREA(RPHASE,NPTP2,NXLO,NYLO,.55,YSCALE)
C       CALL REAREA(RMAG,NPTP2,RPHASE)

C       And now for the magnitude.
        CALL COMMAG(CBUFF1,NPTS/4,RMAG)
        CALL AREREA(RMAG(6+1),5,RMARE1)
        CALL EXTREA(RMAG,NPTS/4,RMIN,RMAX)
        CALL SCAREA(RMAG,NPTS/4,100./RMAX)
        NXLO= NXLO+NPTS +40
C       NYLO= NYLO- YSCALE*100- 30
        CALL BRAKIT(NXLO,NYLO,5,9,30,8.,YSCALE)
        CALL PLTREA(RMAG,NPTS/8,NXLO,NYLO,8.,YSCALE)

C       Leave plot origin at bottom left of next row.
5000    NXO= 30
        NYO= NYO- YSCALE*100 - 60

D       TYPE *,'COSANG[1,2,3]= ',(COSANG(I),I=1,3)
D       TYPE *,'NSYSTO= ',NSYSTO

END
```

```
        .TITLE   MAXAMR
        .ENABL   LC
        .GLOBL   MAXAMR
        .GLOBL   SRKMBA, PRCENT, MEDIAN, SWABTS, GTBYT
        .GLOBL   SRTMIF

;   MAXAMR --
;       FORTRAN callable subroutine to return a resistant estimate of
;       the mode (tends to ignore outliers in a non-linear fashion). It
;       functions as follows:
;       1)  Sort the spectrum on the input data, after putting the
;           original order in the upper byte of each word.
;       2)  Take the upper "NROBUS" elements, or until the "NOISE"
;           level is reached, or until "LIMIT" % of the overall
;           maximum is reached and . . .
;       3)  . . . return the median of this bunch as the mode.

;   On Entry --
;       The input file is assumed to be positioned at the beginning
;   of the spectrum (or whatever) to be scrutinized.
;           2(R5) is address of the array having the spectrum.
;           @4(R5) is the number of elements (words) in the array.
;           @6(R5) is the "amount of robustness" desired. It will determine
;   the maximum number of data points to consider in making the estimate.

;   On Exit --
;       The integer estimate is returned @8.(R5).
;       The input file is advanced to the byte following the array
;   just analyzed.

;   Assembler constants.
LIMIT       = 50.
NOISE       = 5.

MAXAMR:
;   Force reasonable values for input parameters.
        TST      @4(R5)
        BGE      1$
        CLR      @4(R5)
1$:
        TST      @6(R5)
        BGE      2$
        CLR      @6(R5)
2$:
```

```
            ;"R" value to R4, where it will stay.
            MOV     @6(R5),R4

;   Put frequency indices in the upper bytes of the input array.
            MOV     2(R5),R1            ;R1:= address of array.
            MOV     @4(R5),R2           ;R2:= no. of elements in array.
            CLR     R3                  ;R3:= freq. index.

SETKY:
            MOVB    (R1),R0             ;Next datum to R0.
            SWAB    R0                  ;Put upper byte in position.
            BIS     R3,R0               ;Mask in the freq. index.
            SWAB    R0                  ;Restore order.
            INC     R3                  ;Next freq.
            MOV     R0,(R1)+            ;Store result in the array.
            SOB     R2,SETKY            ;Loop until done.
            MOV     R1,-(SP)            ;Save the end point.
    ;   Sort the array from smallest to largest.
            MOV     2(R5),R1
            MOV     @4(R5),R2
            CALL    SRKMBA ;   Compute the cutoff amplitude.
            MOV     (SP),R2             ;Restore end of array.
            DEC     R2
            MOVB    -11.(R2),R1         ;R1:= maximum amplitude.
            MOV     #NOISE,R3           ;R3:= Level below which data is noise.
            MOV     #LIMIT,R0
            CALL    PRCENT              ;R0:= threshold amplitude.

;   Descend through the list.
            MOV     -1(R2),R1
            MOVB    R1,R2
            ASH     #-2,R2              ;R2:= Max. amp/8
            ADD     R2,R4               ;Increase "R" by (Max amp)/8.
            MOV     R4,R2               ;R2:= no. of points to consider.
            MOV     (SP)+,R1            ;Start at maximum.

DESCND:
            TST     -(R1)
            CMPB    (R1),R3             ;Below noise ?
            BLE     ESTIMA              ;Yes.
            CMPB    (R1),R0             ;Below threshold ?
            BLE     ESTIMA              ;Yes.
            SOB     R2,DESCND
```

;   Compute the estimate.  R1 addresses the point where the descent
;   stopped.  R4 +1 -R2 gives the no. of points in the estimate.
ESTIMA:
        SUB     R4,R2
        NEG     R2              ;R2:= no. of points in the estimate.
        INC     R2              ;Make sure there's at least one.
        CALL    SWABTS          ;Swap all the byte pairs.

;   Sort according to frequency.
        CALL    SRKMBA

;   Return the median.
        CALL    MEDIAN
;       BIC     #177400,R0
        MOVB    R0,R0
        MOV     R0,@8.(R5)

RETURN

.END
        .TITLE  LIMITS
        .ENABL  LC
        .GLOBL  LIMITS
        .GLOBL  SRKMBA,MEDIAN,SWABTS,WINEST

;   LIMITS --
        Computes a robust estimate of the high and low contours of
;   a spectrum about the location point.

;   On Entry --
;       @2(R5)= Location estimator.
;       @4(R5)= Threshold or contour level.
;       6(R5)= Addresses the integer array with the spectrum
;   having frequency indices in the upper bytes of each element.
;       @8(R5)= No. of elements in the spectrum array.
;       @10(R5)= Robustness.

;   On Exit --
;       @12(R5)= Lower limit.
;       @14(R5)= Upper limit.

;   Assembler constants.
NOISE   = 1.

LIMITS:
;   Put the threshold in R3.
         MOV    @4(R5),R3
         CMP    R3,#NOISE         ;Threshold into noise margin ?
         BGE    1$                ;No.
         MOV    #NOISE,R3         ;Yes, up the threshold.
1$:
;   Compute address of location point.
         MOVB   @2(R5),R1
         ASL    R1                ;Convert to byte count.
         ADD    6(R5),R1
         MOV    R1,R2             ;R1 & R2 both address location point.

;   Search from location point downward to find low limit.
         MOVB   @2(R5),R4
         BEQ    LOWDNE
         TST    (R1)+
         ADD    #2,R4             ;R4:= Distance to minus infinity.

LOWSEA:
         DEC    R4
         BLT    LOWDNE            ;Test for end of buffer.
         DEC    R1
         CMPB   -(R1),R3
         BGE    LOWSEA LOWFND:
;        Check for consistency in next point.
         MOV    R1,R0
         DEC    R0
         CMPB   -(R0),R3          ;Next point < threshold ?
         BGE    LOWSEA            ;No, keep searching.

LOWDNE:
;   Search from location point upward to find high limit.
         MOV    @8.(R5),R4
         MOVB   @2(R5),R0
         SUB    R0,R4
         SUB    #2,R4             ;R4:= Distance to plus infinity.
         BEQ    HIDNE
         TST    -(R2)

HISEA:
         DEC    R4
         BLT    HIDNE             ;Test for end of buffer.

```
        TST     (R2)+           ;Advance index ptr. to next word.
        CMPB    (R2), R3        ;Below threshold ?
        BGE     HISEA           ;No, check the next.

HIFND:
;       Check for consistency in next point.
        DEC     R4
        BLT     HIDNE           ;Test for end of buffer.
        TST     (R2)+           ;Advance index ptr. to next word.
        CMPB    @R2,R3          ;Next point < threshold ?
        BGE     HISEA           ;No, keep searching.
        TST     -(R2)           ;Yes, correct for extra increment.

HIDNE:

;       Convert R1 & R2 to index values.
        SUB     6(R5),R2
        SUB     6(R5),R1

;       Return low & high limits.
        ASR     R1              ;Convert from byte to ...
        ASR     R2              ;... element count.
        MOV     R1,@12.(R5)
        MOV     R2,@14.(R5)

RETURN

.END

SUBROUTINE MARKS (BUFF, NPTS, NDELX, NX, NY, XSCALE,
        YSCALE, & N1MAX1, N1MIN1, N1ZRO1, R1ARE1, NSYSTO,
        R1ARE2) BYTE BUFF(1)

C       Computes some interesting landmark information
C       from the sequence in "BUFF" which is assumed to
C       have a first derivative function in it.

C       Find maximum acceleration point in the systolic region.
        CALL EXTBYT(BUFF(50), 120, N1MIN1, N1MAX1)
        N1MIN1= N1MIN1+50
        N1MAX1= N1MAX1+50

C       Find the supposed systolic peak. This is defined to be the
C       first near-zero slope point following N1MAX1.
```

```
        DO 400, NSYSTO=N1MAX1, N1MIN1
            IF ( (BUFF(NSYSTO) . LE. BUFF(N1MIN1)+1)
     &        . OR. (BUFF(NSYSTO) . LT. 1) ) GO TO 500
400     CONTINUE
500     CONTINUE

C       Find other extrema now that NSYSTO is defined.
        NSEARC= NSYSTO+10
        CALL EXTBYT(BUFF(NSEARC), 65, N1MIN1, N1MAX1)
        N1MIN1= N1MIN1+NSEARC
        N1MAX1= N1MAX1+NSEARC
        CALL EXTBYT(BUFF((NPTS/2)+1), NPTS/2, N1MIN2, N1MAX2)
        N1MIN2= N1MIN2+NPTS/2
        N1MAX2= N1MAX2+NPTS/2

C       Find the first zero slope point after the max deceleration
C       point (N1MIN1), which is hopefully the first zero slope
C       point following systole.
        DO 600, N1ZRO1=N1MIN1, 200
            IF (BUFF(N1ZRO1) .GT. -1) GO TO 700
600     CONTINUE
700     CONTINUE C       Compute the area under the post systolic deceleration
C       curve at the point of greatest deceleration.
        R1ARE1=0
        R1ARE2=0
        DO 300, I=N1MIN1-10, N1MIN1+10
            II=BUFF(I)
            IF(II .LT. 0) R1ARE2= R1ARE2 + II
300         R1ARE1=R1ARE1+BUFF(I)
        R1ARE1= R1ARE1/FLOAT(NDELX)
        R1ARE2= R1ARE2/FLOAT(NDELX)

C       Write bars out to the plot so people can see what happened.
        CALL BRAKIT (NX, NY, N1MIN1, N1MAX1, 90, XSCALE, YSCALE)
        CALL BRAKIT (NX, NY, NSYSTO, N1ZRO1, 100, XSCALE, YSCALE)

END

SUBROUTINE BFEATU(LOCBUF, SCLBUF,
     &      NPTS, YSCALE, NXO, NYO, CBUFF1, CBUFF2, NROBUS,
            NCYCMX, PATNAM) COMMON /MARKS/NOMIN1, NOAMAX1,
            NOMIN2, NOMAX2, N1MIN1, N1MAX1, & N1MIN2, N1MAX2,
```

```
      NSYSTO, N1ZRO1
      COMMON /PARAMS/AREA, COSANG(3), SINANG(3),
     &    ROVAL1,ROVAL2,ROARE1,ROARE2,
     &    R1VAL1,R1VAL2,R1ARE1,R1ARE2,
     &    RMVAL1,RMVAL2,RMARE1,RMARE2,
     &    RPVAL1,RPVAL2,RPARE1,RPARE2,
     &    SLOPE
      COMMON /ARRAYS/SCR1,SCR2,SCR3,RTIME,RMAG,RPHASE

VIRTUAL CBUFF1(1),CBUFF2(1)
      COMPLEX CBUFF1,CBUFF2,CTEMP
      REAL RTIME(512),RMAG(512),RPHASE(512),FEATS(1)
      BYTE PATNAM(1)
      BYTE LOCBUF(1),SCLBUF(NPTS, 1)
      BYTE SCR1(512),SCR2(512),SCR3(512),NOTCHS(2)
      PI2= 3. 14159265*2
      NPTP2= 512
      XSCALE= YSCALE/3.

C     Copy location data to scratch 1, real, and complex buffers.
      CALL STCOPY(LOCBUF,SCR1,NPTS)

C         Force effective end of data to occur at t= .5 sec.
          CALL INIBYT(LOCBUF(240),41,LOCBUF(240))
          CALL INIBYT(SCLBUF(240,1),41,SCLBUF(240,1))
          CALL INIBYT(SCLBUF(240,2),41,SCLBUF(240,2))
          CALL INIBYT(SCLBUF(240,3),41,SCLBUF(240,3))
          CALL INIBYT(SCLBUF(240,4),41,SCLBUF(240,4))

C     Substract off the DC offset in the input data.
      CALL ADDBYT(SCR1,NPTS,-30)
      CALL ADDBYT(LOCBUT,NPTS,-30)
      DO 100, I=1,4

100       CALL ADDBYT(SCLBUF(1,I),NPTS,-30)

C     Remove the ECG trigger spike.
      SCR1(41)= SCR1(40)
      LOCBUF(41)= LOCBUF(40)
      DO 110,I=1,4
110       SCLBUF(41,I)= SCLBUF(40,I)

CALL DOTIME(LOCBUF,SCLBUF,NPTS,RTIME,NPTP2,AREA,
      PATNAM) IF (AREA . GT. 0.0) GO TO 120
          PRINT 111,(PATNAM(I),I=1,8)
```

```
     111         FORMAT(' BFEATU-W-',8A1,' has zero energy')
                 GO TO 5000
     120         CONTINUE
         C       Plot the location data.
                 CALL PLTRE1(NXO, NYO, O, IFIX(30*YSCALE),
             &       XSCALE, YSCALE, RTIME, 280, NROBUS, NCYCMX, PATNAM)

C       Initialize plotting coordinates.
                 NXLO= NXO+NPTS +40
                 NYLO= NYO- 30*YSCALE CALL SCAREA(RTIME, 512, 1. /AREA)
                 CALL REACOM(RTIME, NPTP2, CBUFF1)

C       Find land marks in the velocity waveform.
         C       (Use "SCR1" data for extrema since it has +.6 sec data intact).

CALL EXTBYT(SCR1, (NPTS/2)+30,NOMIN1,NOMAX1)
                 CALL EXTBYT(SCR1( (NPTS/2)+1 ), NPTS/2,NOMIN2,NOMAX2)
                 NOMIN2= NOMIN2+ NPTS/2
                 NOMAX2= NOMAX2+ NPTS/2

CALL BRAKIT(NXO, NYO, (NOMAX1-1), (NOMIN2-1), 35,
                 XSCALE, YSCALE)

C       Compute first derivative and leave in scratch 3.
                 NDELX= 9 ! set delta X.
                 CALL DERIV(LOCBUF, NPTS, NDELX, SCR2)
                 CALL SMOOTH(SCR2, NPTS, 4, SCR3)
                 CALL MARKS(SCR3, NPTS, NDELX, NXLO, NYLO, 1., YSCALE,
                 & N1MAX1, N1MIN1, N1ZRO1, R1ARE1, NSYSTO, R1ARE2)
                 CALL BRAKIT(NXO, NYO, NSYSTO, N1ZRO1, 40, XSCALE,
                 YSCALE)
                 CALL SCABYT(SCR3, NPTS, 2.5)
                 CALL ADDBYT(SCR3, NPTS, 50)
                 CALL PLTBYT(SCR3, NPTS, NXLO, NYLO, 1., YSCALE)

NXFIL= NXO
                 NYFIL= NYO-100*YSCALE-20

C       Compute the DFT and display the magnitude.
                 CALL HAMEND(CBUFF1, NPTP2)
                 CALL FFTFOR(NPTS, CBUFF1)
```

```
C              Phase to "RPHASE".
               DO 200, I=1, NPTP2
200                RPHASE(I)= AIMAG( CLOG( 1. OE-6+CBUFF1(I) ) )
C              Unwrap the phase.
               DO 400, I=1, 511
                   NDIFF= ( ABS(RPHASE(I+1) - RPHASE(I))/PI2 ) + .5
                   IF ( RPHASE(I+1) . LT. RPHASE(I) ) NDIFF= -NDIFF
400                RPHASE(I+1)= RPHASE(I+1) - PI2*NDIFF
               SLOPE= -2*RPHASE( (NPTP2/2)+1 )
               DO 450, I=1, NPTP2
450                RPHASE(I)= RPHASE(I) + SLOPE*(I-1)/NPTP2

C              CALL REAREA(RPHASE, NPTP2, RMAG)
C              CALL EXTREA(RPHASE, NPTP2, RMIN, RMAX)
C              CALL SCAREA(RPHASE, NPTP2, 50./(AMAX1(ABS(RMAX),
               ABS(RMIN))) )
C              CALL ADDREA(RPHASE, NPTP2, 50.)
C              NXLO= NXLO+NPTS +40
C              CALL PLTREA(RPHASE, NPTP2, NXLO, NYLO,. 55, YSCALE)
C              CALL REAREA(RMAG, NPTP2, RPHASE)

C              And now for the magnitude.
               CALL COMMAG(CBUFF1, NPTS/4, RMAG)
               CALL AREREA(RMAG(6+1), 5, RMARE1)
               CALL EXTREA(RMAG, NPTS/4, RMIN, RMAX)
               CALL SCAREA(RMAG, NPTS/4, 100./RMAX)
               NXLO= NXLO+NPTS +40
C              NYLO= NYLO- YSCALE*100- 30
               CALL BRAKIT(NXLO, NYLO, 5, 9, 30, 8., YSCALE)
               CALL PLTREA(RMAG, NPTS/8, NXLO, NYLO, 8., YSCALE)

C              Leave plot origin at bottom left of next row.
5000           NXO= 30
               NYO= NYO- YSCALE*100 - 60

D              TYPE *, 'COSANG[1, 2, 3]= ',(COSANG(I), I=1, 3)
D              TYPE *, 'NSYSTO= ',NSYSTO

END
```

While preferred embodiments of the invention have been shown and described, those skilled in the art will recognize variations, modifications, and alterations that might be made to the embodiments without departing from the inventive concept. The claims should be construed liberally in view of the description to cover the preferred embodiments of the invention and their reasonable equivalents. The claims should not be limited to the particular embodiments described, unless such limitations is necessary in view of the pertinent prior art.

We claim:

1. A noninvasive method for diagnosing the degree of vessel stenosis in a patient comprising the steps of:
   (a) comparing patient blood flow data, based upon time domain and frequency domain ultrasound Doppler shift information obtained at a Doppler angle $\theta$ defined with respect to the patient's common and internal carotid arteries, with corresponding reference blood flow data, characteristic of a test group of people whose common and internal carotid arteries have been independently evaluated for stenosis, the blood flow having characteristic regions designated systole, diastole, early diastole, late distole, and dicrotic notch, the patient blood flow data and corresponding reference blood flow data being compared defining a first set that includes information indicative of:
      (1) the logarithm of the product of the reciprocal of cos $\theta$ and the mean blood flow in the common carotid artery during early diastole;
      (2) the reciprocal of cos $\theta$ multiplied by the change in the blood flow frequency in the common carotid artery after systole, the product of which is raised to the fourth power;
      (3) the logarithm of the mode blood flow frequency in the internal carotid artery;
      (4) the minimum point on a signal contour, which is separated by approximately 9 dB from a contour representing the mode blood flow frequency in the internal carotid artery, raised to the fourth power; and
      (5) the logarithm of the product of the reciprocal of cos $\theta$ and the mean blood flow in the common carotid artery during later diastole; and
   (b) producing a diagnosis output, the diagnosis output indicating a diseased condition when the patient blood flow data and corresponding reference blood flow data have a first relationship and indicating a normal condition when the patient blood flow data and corresponding reference blood flow data have a second relationship.

2. The method of claim 1, wherein the patient blood flow data and corresponding reference blood flow data being compared further define a second set including information indicative of:
   (a) the peak point on a signal contour, which is separated by approximately 9 dB from a contour representing the mode blood flow frequency in the internal carotid artery, raised to the second power;
   (b) the maximum frequency, between approximately ±50 msec of the systolic peak, on a signal contour that is approximately 9 dB below a contour representing the mode blood flow frequency in the internal carotid artery, raised to the fourth power;
   (c) the reciprocal of cos $\theta$ multiplied by the change in blood flow frequency in the internal carotid artery after systole;
   (d) the logarithm of the first minimum of the blood flow frequency in the internal carotid artery; and
   (e) the width of a signal contour that is approximately 9 dB above a contour representing the mode blood flow frequency in the internal carotid artery approximately 50 msec after systole, raised to the fourth power; and wherein the diagnostic output further indicates a greater than 50 percent stenosis condition when the second set of patient blood flow data has a third relationship to the second set of reference blood flow data and indicates a less than 50 percent stenosis condition when the second set of patient blood flow data has a fourth relationship to the second set of reference blood flow data.

3. The method of claim 2, wherein the patient blood flow data and corresponding reference blood flow data being compared further define a third set including information indicative of:
   (a) the peak point on a signal contour that is separated by approximately 9 dB from a contour representing the mode blood flow frequency in the internal carotid artery;
   (b) the logarithm of the blood flow frequency in the common carotid artery approximately 125 msec before the dichnotic notch;
   (c) the logarithm of the product of the reciprocal of cos $\theta$ and the change in the blood flow frequency in the internal carotid artery at systole; and
   (d) the logarithm of a signal contour that is approximately 9 dB below a contour representing the mode blood flow frequency in the internal carotid artery; and wherein the diagnostic output further indicates a greater than 35 percent stenosis condition when the third set of patient blood flow data has a fifth relationship to the third set of reference blood flow data and less than 35 percent stenosis condition when the third set of patient blood flow data has a sixth relationship to the third set of reference blood flow data.

4. The method of claim 3, wherein the patient blood flow data and corresponding reference blood flow data being compared each further define a fourth set including:
   (a) the logarithm of the area under a blood flow frequency curve for an interval of approximately ±37.5 msec around systole in the common carotid artery;
   (b) the logarithm of the peak point on a signal contour that is separated by approximately 9 dB from a contour representing the mode blood flow frequency in the internal carotid artery;
   (c) the peak point on a signal contour that is separated by approximately 9 dB from a contour representing the mode blood flow frequency in the internal carotid artery;
   (d) the width of a signal contour that is approximately 9 dB above a contour representing the mode blood flow frequency in the common carotid artery approximately 125 msec after distole; and
   (e) the logarithm of the width of a signal contour that is approximately 3 dB below a contour representing the mode blood flow frequency in the internal carotid artery approximately 125 msec after diastole; and wherein, the diagnostic output further indicates a greater than 15 percent stenosis condition when the fourth set of patient blood flow data has a seventh relationship to the fourth set of reference blood flow data and has a less than 15 percent stenosis condition when the fourth set of patient blood flow data has an eighth relationship to the fourth set of reference blood flow data.

* * * * *